(12) United States Patent
Giannini et al.

(10) Patent No.: US 8,383,616 B2
(45) Date of Patent: Feb. 26, 2013

(54) ARYL ISOXAZOLE COMPOUNDS WITH ANTITUMOURAL ACTIVITIES

(75) Inventors: Giuseppe Giannini, Pomezia (IT); Walter Cabri, Rozzano (IT); Daniele Simoni, Ferrara (IT); Riccardo Baruchello, Ferrara (IT); Paolo Carminati, Milan (IT); Gabriella Singrossi, legal representative, Milan (IT); Silvia Carminati, legal representative, Milan (IT); Giuseppe Paolo Carminati, legal representative, Milan (IT); Claudio Pisano, Aprilia (IT)

(73) Assignee: Sigma-Tau Industrie Farmaceutiche Riunite SpA, Rome (IT)

( * ) Notice: Subject to any disclaimer, the term of this patent is extended or adjusted under 35 U.S.C. 154(b) by 0 days.

(21) Appl. No.: 13/001,652

(22) PCT Filed: Jun. 30, 2009

(86) PCT No.: PCT/EP2009/058205
§ 371 (c)(1),
(2), (4) Date: May 2, 2011

(87) PCT Pub. No.: WO2010/000748
PCT Pub. Date: Jan. 7, 2010

(65) Prior Publication Data
US 2011/0245221 A1    Oct. 6, 2011

(30) Foreign Application Priority Data
Jul. 4, 2008   (EP) .................................. 08159692

(51) Int. Cl.
| A61K 31/397 | (2006.01) |
| A61K 31/5377 | (2006.01) |
| A61K 31/497 | (2006.01) |
| A61K 31/4468 | (2006.01) |
| A61K 31/422 | (2006.01) |
| A61K 31/42 | (2006.01) |
| C07D 413/12 | (2006.01) |
| C07D 403/12 | (2006.01) |
| C07D 401/12 | (2006.01) |
| C07D 261/18 | (2006.01) |

(52) U.S. Cl. ............. 514/210.2; 514/236.8; 514/254.04; 514/326; 514/380; 544/137; 544/367; 546/209; 548/245

(58) Field of Classification Search ........................ None
See application file for complete search history.

(56) References Cited

FOREIGN PATENT DOCUMENTS
| WO | 2004/072051 | 8/2004 |
| WO | 2007/096194 | 8/2007 |

OTHER PUBLICATIONS

Brough, P. et al., "4, 5-Diarylisoxazole Hsp90 Chaperone Inhibitors: Potential Therapeutic Agents for the Treatment of Cancer" Journal of Medicinal Chemistry, vol. 51, Nov. 20, 2007, pp. 196-218.

Primary Examiner — Rebecca Anderson
Assistant Examiner — Alicia L Otton
(74) Attorney, Agent, or Firm — Lucas & Mercanti, LLP

(57) ABSTRACT

The present invention relates to formula I compounds having antitumoural activities through, as one possible biological target, the molecular chaperone heat shock protein 90 (Hsp90) inhibition. The invention includes the use of such compounds in medicine, in relation to cancer disease as well as other diseases where an inhibition of Hsp90 is responsive, and the pharmaceutical compositions containing such compounds.

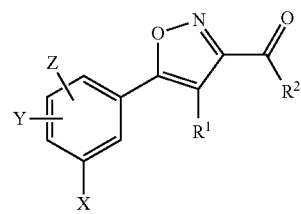

16 Claims, No Drawings

ARYL ISOXAZOLE COMPOUNDS WITH ANTITUMOURAL ACTIVITIES

CROSS-REFERENCE TO RELATED APPLICATIONS

This application is a 371 of PCT/EP2009/058205 filed on Jun. 30, 2009, which claims the benefit of European Patent Application No. 08159692.6 filed on Jul. 4, 2008, the contents of each of which are incorporated herein by reference.

FIELD OF THE INVENTION

The present invention relates to aryl isoxazole derivatives having antitumoural activities through, as one possible biological target, the molecular chaperone heat shock protein 90 (Hsp90) inhibition. The invention includes the use of such compounds in medicine, in relation to cancer disease as well as other diseases where an inhibition of HSP90 is responsive, and the pharmaceutical composition containing such compounds.

BACKGROUND OF THE INVENTION

Heat shock proteins (Hsp's) play a key role in cell protection against various cell stress factors (i.e. toxic xenobiotic, chemotherapy, radiation) acting as a protective factor against the misfolding of essential proteins involved in maintaining cell functionality. Hsp90 proteins, members of these molecular chaperones are proteins that play a key role in the conformational maturation, stability and function of so-called "client" proteins, many of them belonging to the oncogenic protein family, such as Bcr-Abl, p53, Raf-1, Akt/, ErbB2, EGFR, Hif and other proteins, as well as steroid hormone receptors. The inhibition of Hsp90 triggers the disruption of the Hsp90-client protein complex, and subsequently, its proteasome-mediated degradation causes loss of function and inhibition of cell growth. Interestingly, heat shock protein 90 has emerged as an important target in several diseases. In particular, the role played by Hsp90 in regulating and maintaining the transformed phenotype in cancers and neurodegenerative diseases has been recently identified, as well as its roles in fungal and viral infections (Solit D. B., et al., *Drug Discov. Today*, 2008, 13(1-2), 38). In particular, Hsp90 inhibition has also been reported to be beneficial in the treatment of neurodegenerative diseases such as dementia with Lewy bodies, amyotrophic lateral sclerosis, spinal and bulbar muscular atrophy, spinocerebellar ataxias, Parkinson, Huntington and Alzheimer's diseases (Taylor D. M., et al., Cell Stress Chaperones, 2007, 12, 2, 151; Yang Z., et al., *Nat. Med.*, 2007, 13, 3, 348; Katsuno M., et al., *Proc. Natl. Acad. Sci. USA*, 2005, 12, 46, 16801; Gallo K. A., *Chem. Biol.*, 2006, 13, 115; Luo W., et al., *Proc. Natl. Acad. Sci.*, 2007, 104, 9511; Macario A. J., et al., *N. Engl. J. Med.*, 2005, 353, 1489; Dou F., et al., *Int. J. Mol. Sci.*, 2007, 8, 51); inflammatory diseases (Vega V. L., et al., *Mol. Biol. Cell.*, 2003, 14, 764; Poulaki V., et al., *Faseb J.*, 2007, 21, 2113); cerebral ischemia (Lu A., et al., *J. Neurochem.*, 2002, 81, 2, 355) and malaria (Kumar R., et al., *J. Biosci.*, 2007, 32, 3, 531).

Moreover, many Hsp90 client proteins are over-expressed in cancer, often in mutated forms, and are responsible for unrestricted cancer cell proliferation and survival. Interestingly, Hsp90 derived from tumour cells has particularly high ATPase activity with higher binding affinity to Hsp90 inhibitors than the latent form in normal cells, allowing specific targeting of Hsp90 inhibitors to tumour cells with little inhibition of Hsp90 function in normal cells (Chiosis G., et al., ACS Chem. Biol., 2006, 1, 5, 279). In addition, Hsp90 has also been recently identified as an important extracellular mediator for tumour invasion (Eustace B. K., et al., *Nature Cell Biol.*, 2004, 6, 6, 507; Koga F., et al., *Cell cycle*, 2007, 6, 1393).

Thus, Hsp90 is considered a major therapeutic target for anticancer drug development because inhibition of a single target represents attack on all of the hallmark traits of cancer.

Since the discovery that two natural compounds, geldanamycin and radicicol, were able to inhibit Hsp90 function through binding to an ATP binding pocket in its N-terminal domain, the interest for Hsp90 inhibitors has grown. The natural antibiotic geldanamycin was shown to exhibit potent antitumour activity against human cancer cells (Whitesell L., et al., *Cancer Res.*, 1992, 52, 1721), but significant toxicity prevented its clinical development (Supko J. G., et al., *Cancer Chemother. Pharmacol.*, 1995, 36, 305).

The first-in-class Hsp90 inhibitor to enter clinical trials was the geldanamycin analogue 17-AAG (17-allylaminogeldanamycin). Even though high in vitro activity characterizes this geldanamycin derivative, its interest is shadowed by poor solubility coupled to hepatotoxicity properties. Some of these problems have been partially solved by the discovery of 17-dimethylaminoethylgeldanamycin.

Radicicol, a natural macrocyclic anti-fungal antibiotic, was found to inhibit Hsp90 protein by interacting at a different site of action than Geldanamycin (Sharma S. V., et al., *Oncogene*, 1998, 16, 2639). However, due to its intrinsic chemical instability it was deprived of in vivo activity.

Another important class of inhibitors resides in the purine scaffold. This class of derivatives was devised by structural homology with ATP. Among the many inhibitors developed within this family, PU24FCl was found to possess high in vitro and in vivo activity (He H., et al., *J. Med. Chem.*, 2006, 49, 381).

High-throughput screening campaigns permitted the discovery of benzisoxazole derivatives endowed of Hsp90 inhibitory properties having a resorcinol moiety in position 3 (Gopalsamy A., et al., *J. Med. Chem.*, 2008, 51, 373).

Among the different class of Hsp90 inhibitors, Vernalis Ltd. has disclosed 4,5-diarylpyrazoles (Cheung K. M., et al., *Bioorg. Med. Chem. Lett.*, 2005, 15, 3338); 3-aryl,4-carboxamide pyrazoles (Brough P. A., et al, *Bioorg. Med. Chem. Lett.*, 2005, 15, 5197), 4,5-diarylisoxazoles (Brough P. A., et al., *J. Med. Chem.*, 2008, 51, 196), 3,4-diaryl pyrazole resorcinol derivative (Dymock B. W., et al., *J. Med. Chem.*, 2005, 48, 4212; Smith N. F., et al., *Mol. Cancer Ther.*, 2006, 5, 6, 1628) and thieno[2,3-d]pyrimidine (WO2005034950, AACR 2009, Denver, Colo., poster 4684).

WO2003013517 reports 3-aryl-5-aminoisoxazole derivatives as kinase inhibitors useful as anticancer agents.

WO2002070483 discloses heterocyclic diamide compounds of general formula I as useful agents for controlling invertebrate pest.

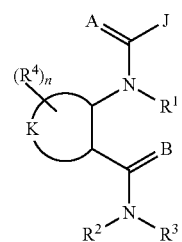

Formula 1

However, to date, no Hsp90 inhibitors fully satisfy the requisites of safety and stability. Therefore, the desire of potent and selective Hsp90 inhibitors remains an interesting and promising goal. We have now found that 4-amino substituted aryl isoxazole are endowed of high and unexpected Hsp90 inhibitory properties.

DESCRIPTION OF THE INVENTION

The present invention relates to a new class of substituted 4-amino-5-aryl isoxazole compounds and its use as Hsp90 inhibitors. A core isoxazole ring with one aromatic substitution on position 5, and a limited class of amido substitution on position 3, associated to a NH-substitution like amine, amide, ureido, carbamate, etc. on position 4 are the principle characterising features of the compounds of the present invention.

The invention provides compounds of formula (I) or a salt, N-oxide, hydrate or solvate thereof, in the preparation of a composition for inhibition of Hsp90 activity:

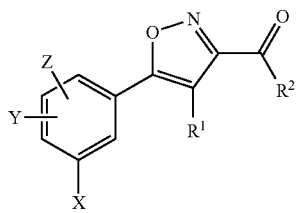

Formula I wherein,
X is halogen, alkyl, alkenyl, haloalkyl, aryl, heteroaryl, benzyl, amino, alkylamino, or aminocarbonyl;
Y and Z, the same or different, are halogen, nitro, haloalkyl, $R^3$, $OR^3$, amino, alkylamino, or aminocarbonyl;
$R^3$ is hydrogen, alkyl;
$R^1$ is NHC(=D)E$R^4$ or $NR^5R^6$;
D is O or S;
E is O, $NR^7$ or is absent;
$R^7$ is hydrogen or alkyl;
$R^4$ is alkyl optionally substituted once with alkoxy or amino; alkenyl, aryl optionally substituted once or more with alkoxy, halo or heterocycloalkylalkyl; cycloalkyl optionally substituted once or more with alkyl, haloalkyl, alkoxy, amino or aminoalkyl; norbornyl, adamantyl, heteroaryl optionally substituted once or more with alkyl, alkylaminocarbonyl; heterocycloalkyl optionally substituted once or more with alkyl; or heterocycloalkylalkyl optionally substituted once or more with alkyl;
$R^5$ and $R^6$ independently are hydrogen, alkyl, cycloalkyl, heterocycloalkyl optionally substituted once or more with alkyl; alkenyl, benzyl, aryl, arylkyl optionally substituted with alkoxy; heteroaryl, heteroarylkyl optionally substituted once or more with alkyl, hydroxyalkyl, alkoxy, alkoxycarbonyl; or $R^5$ and $R^6$ taken together with the nitrogen atom to which they are attached can form an optionally substituted 5 to seven-membered heterocycle ring, which optional substitution being halogen, hydroxyl, alkoxyl, alkyl, aryl, arylkyl, alkylcarbonyl or aminocarbonyl.
$R^2$ is $NR^8R^9$;
$R^8$ and $R^9$, the same or different are chosen from H, alkyl optionally substituted with halogen; haloalkyl, aryl, cycloalkyl, heterocycloalkyl and heteroaryl; or $R^8$ and $R^9$, taken together with the nitrogen atom to which they are attached, form a heterocycle that may contain one or two further heteroatoms selected from O, S or N and which can optionally be substituted once or twice with alkyl or halogen;

their tautomers, their geometrical isomers, their optically active forms such as enantiomers, diastereomers and their racemate forms, as well as their pharmaceutically acceptable salts thereof.

An embodiment of this invention is that of compounds of formula I, for use as medicaments.

In a further embodiment, said medicament is used for treating a subject afflicted by cancer diseases, neurodegenerative diseases, inflammatory diseases, cerebral ischemia or malaria.

In a preferred embodiment, said medicament is used for treating cancer diseases.

In another preferred embodiment, said medicament is used for treating inflammatory diseases.

In another still preferred embodiment, said medicament is used for treating autoimmune diseases.

In a still preferred embodiment, said medicament is used for treating cerebral ischemia.

In another still preferred embodiment, said medicament is used for treating parasitemia including malaria.

The invention furthermore provides a process for the preparation of compounds of formula I, which can be prepared by conventional synthetic methods and are described underneath.

Compounds of formula I, where $R^4$ is NHC(=D)E$R^4$, D is O and E is absent, can be obtained for example by reacting a compound of formula II,

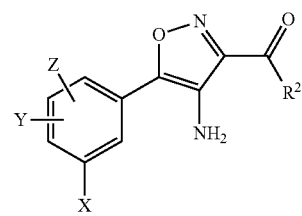

Formula II wherein X, Y, Z and $R^2$ are as described above, with an acyl chloride of formula ClCO$R^4$ in an aprotic solvent (i.e., DCM) in the presence of a base such as $NEt_3$. Corresponding compounds where D is S can be obtained by reacting the latter with the Lawesson's reagent in toluene at a temperature ranging from RT to 90° C.

Compounds of formula I, where $R^1$ is $NR^5R^6$ and where $R^5$ and $R^6$ are alkyl, cycloalkyl, heterocycloalkyl, arylkyl or heteroarylkyl can be obtained for example by reacting a compound of formula II, wherein X, Y, Z and $R^2$ are as described above, with one or more equivalents of compounds of formula R—CHO or R'=O (with the meaning of ketone), where the moieties R—C and R' have the meaning of $R^5$ and/or $R^6$ as described above, in a polar solvent (i.e., MeOH) in the presence of an acid such as AcOH and of a reducing agent such as $NaCNBH_4$.

Alternatively, compounds of formula I, where $R^1$ is $NR^5R^6$ and where $R^5$ and $R^6$ are alkyl, alkenyl, arylkyl or heteroarylkyl can be obtained for example by reacting a compound of formula II, wherein X, Y, Z and $R^2$ are as described above, with one or more equivalents of compounds of formula R—X', where R has the meaning of $R^5$ and/or $R^6$ as described above, and $X^1$ has the meaning of a leaving group such as Cl, Br or Tf, in an aprotic solvent (i.e., DCM) in the presence of a base such as $NEt_3$.

Alternatively, compounds of formula I, where $R^1$ is $NR^5R^6$ and where $R^5$ and/or $R^6$ represent aryl or heteroaryl, can be obtained for example by reacting a compound of formula III,

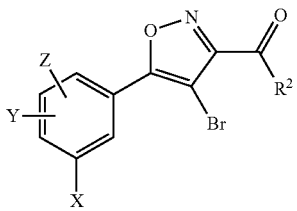

Formula III wherein X, Y, Z and $R^2$ are as described above, with an amine of formula IV

Formula IV where $R^5$ and $R^6$ have the meanings as defined above, in the presence of a catalyst such as $Pd(dba)_2/P(tBu)_3$.

Compounds of formula III can be obtained as described in WO04072051 via bromination of the corresponding 4-H isoxazole derivative with bromine in acetic acid in the presence of sodium acetate.

Compounds of formula I, where $R^1$ is $NHC(=D)ER^4$ can be obtained for example by reacting a compound of formula V,

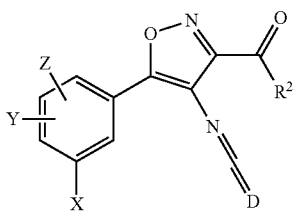

Formula V wherein X, Y, Z, D and $R^2$ are as described above, with a compound of formula $ER^4$, wherein E is $NR^7$ and $R^4$ are as described above, in an aprotic solvent (i.e., THF) in the presence of a base.

Compounds of formula II, wherein X, Y, Z and $R^2$ are as described above, can be obtained for example by reacting compounds of formula VI

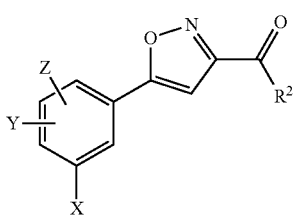

Formula VI wherein X, Y, Z and $R^2$ are as described above,
with $HNO_3/Ac_2O$ to get the nitro-derivatives of formula VII (Chimichi S.; et al., *Heterocycles,* 1989, 29, 1965)

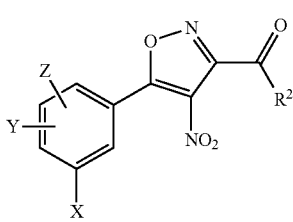

Formula VII wherein X, Y, Z and $R^2$ are as described above which in turn undergoes a reduction process (i.e., by means of $Zn/NH_4Cl$ as reported, Pascual A., *Helvetica Chim. Act.,* 1989, 72, 3, 556).

An embodiment of the present invention is that of compounds of formula VII wherein X, Y, Z and $R^2$ are as described above as an intermediate in the synthesis of compounds of formula I.

Another embodiment of the present invention is that of compounds of formula II wherein X, Y, Z and $R^2$ are as described above as an intermediate in the synthesis of compounds of formula I.

In all said transformations, any interfering reactive group can be protected and then deprotected according to well-established procedures described in organic chemistry (see for example: Greene T. W. and P. G. M. Wuts "Protective Groups in Organic Synthesis", J. Wiley & Sons, Inc., 3rd Ed., 1999) and well known to those skilled in the art.

All said transformations are only examples of well-established procedures described in organic chemistry (see for example: March J., "Advanced Organic Chemistry", J. Wiley & Sons, Inc., 4th Ed., 1992) and well known to those skilled in the art.

The term "alkyl" refers to linear or branched alkyl groups having from 1 to 20 carbon atoms, or preferably, 1 to 12 carbon atoms, or even more preferably 1 to about 6 carbon atoms. Lower alkyl group is exemplified by groups such as methyl, ethyl, n-propyl, isopropyl, n-butyl, isobutyl, neo-butyl, tert-butyl, pentyl, iso-pentyl, n-hexyl and the like. Said "alkyl" can optionally be substituted with one or more possible substituents like hydroxyl, halogen, amino, and the like.

The term "cycloalkyl" refers to a saturated or partially unsaturated (but not aromatic) carbocyclic group of 3 to 10 carbon atoms having a single ring. Examples of "$C_3$-$C_{10}$-cycloalkyl" include cyclopropyl, cyclobutyl, cyclopentyl, cyclohexyl, and the like. Said cycloalkyl can optionally be substituted with one or more hydroxyl, halogen, lower alkyl, haloalkyl, lower alkoxy, amino, aminocarbonyl, alkylcarbonyl or alkoxycarbonyl.

The term "haloalkyl" refers to $CF_3$ or $CHF_2$ moieties or to alkyl groups as previously defined containing $CF_3$ or $CHF_2$ moieties.

The term "alkenyl" refers to linear or branched alkenyl groups preferably having from 2 to 12 carbon atoms, or more preferably, from 2 to 6 carbon atoms also named "lower" alkenyl group and having at least 1 or 2 sites of alkenyl unsaturation. Preferable alkenyl groups include ethenyl (—CH=CH₂), propenyl (allyl, —CH₂CH=CH₂) and the like. The term alkenyl embraces radicals having "cis" and "trans" orientation, or alternatively "Z" and "E".

The term "alkoxy" refers to the group —OR where R includes "alkyl", "cycloalkyl" and "heterocycloalkyl".

The term "alkoxycarbonyl" refers to the group —C(O)OR where R includes "alkyl", "cycloalkyl" and heterocycloalkyl.

The term "amino" refers to the group —$NH_2$.

The term "alkylamino" refers to the group —NHR where R is "alkyl".

The term "cycloalkylamino" refers to the group —NHR where R is "cycloalkyl".

The term "arylamino" refers to the group —NHR where R is "aryl".

The term "aminoalkyl" refers to the group $H_2NR$— where R is "alkylene".

The term "lower" when associated with the terms alkyl, alkoxy, alkylamino, aminoalkyl, or heteroarylkyl, means that the respective alkyl group contains from 1 to 6 carbon atoms.

The terms "heterocycloalkyl" and heterocycle refer to a saturated or partially unsaturated (but not aromatic) four, five-, six- or seven-membered ring containing one or two nitrogen, oxygen or sulfur atoms, which may be the same or different and which rings may be substituted with amino or alkyl. Preferred heterocycloalkyl include azetidine, pyrrolidine, piperidine, piperazine, ketopiperazine, 2,5-diketopiperazine, morpholine and thiomorpholine.

The term "heterocycloalkylalkyl" refers to alkyl groups as defined above, having a heterocycloalkyl substituent; including 2-(1-pyrrolidinyl)ethyl, 4-morpholinyl methyl, 4-morpholinyl ethyl, (1-methyl-4-piperidinyl)methyl, (1-methyl-4-piperazinyl)ethyl and the like.

The term "aryl" refers to an aromatic carbocyclic group of 6 to 14 carbon atoms having a single ring (e.g., phenyl) or multiple rings that may be attached in a pendent manner or may be fused. Preferred aryl include phenyl, naphthyl, phenantrenyl, biphenyl and the like. Said "aryl" may have 1 to 3 substituents chosen among hydroxyl, halogen, haloalkyl, cyano, lower alkyl, lower alkoxy, amino, heterocycloalkylalkyl and lower aminoalkyl or lower alkylamino.

The term "heteroaryl" refers to a monocyclic heteroaromatic, or a bicyclic fused-ring heteroaromatic group. Particular examples of heteroaromatic groups include pyridyl, pyrrolyl, furyl, thienyl, imidazolyl, oxazolyl, isoxazolyl, thiazolyl, isothiazolyl, pyrazolyl, benzofuryl, [2,3-dihydro]benzofuryl, isobenzofuryl, benzothienyl, benzotriazolyl, indolyl and isobenzothienyl. Said "heteroaryl" may have 1 to 3 substituents chosen among hydroxyl, hydroxyalkyl, halo, haloalkyl, nitro, cyano, lower alkyl, lower alkoxy, amino, lower aminoalkyl, lower alkylamino, aminocarbonyl and alkoxycarbonyl.

The term "arylkyl" refers to alkyl groups as defined above, having one or more aryl substituent, including benzyl, phenethyl, diphenyl methyl and the like.

The term "heteroarylkyl" refers to alkyl groups as defined above, having a heteroaryl substituent. Preferred heteroarylkyl are lower heteroarylkyl having the heteroaryl radical attached to a lower alkyl.

The term "aminocarbonyl" refers to the group —C(O)NRR' where each R, R' includes independently H, "alkyl", "alkenyl", "alkynyl", "cycloalkyl", "heterocycloalkyl", "aryl" and "heteroaryl".

We have found that the derivatives (I) and their pharmaceutically acceptable salts, prepared according to the invention, are useful agents for the treatment of disease states, disorders and pathological conditions mediated by Hsp90; in particular for the treatment of cancer diseases, neurodegenerative diseases, inflammatory diseases; cerebral ischemia and malaria.

The pharmaceutical compositions will contain at least one compound of Formula (I) as an active ingredient, in an amount such as to produce a significant therapeutic effect. The compositions covered by the present invention are entirely conventional and are obtained with methods which are common practice in the pharmaceutical industry, such as, for example, those illustrated in Remington's Pharmaceutical Science Handbook, Mack Pub. N.Y.—last edition. According to the administration route chosen, the compositions will be in solid or liquid form, suitable for oral, parenteral or topical administration. The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

Generally, the compounds of this invention are administered in a "therapeutically effective amount". The amount of the compound actually administered will typically be determined by a physician, in the light of the relevant circumstances, including the condition to be treated, the chosen route of administration, the actual compound administered, drug combination, the age, body weight, and response of the individual patient, the severity of the patient's symptoms, and the like. For any compound, the therapeutically effective dose can be estimated initially either in cell culture assays or in animal models, usually mice, rats, guinea pigs, rabbits, dogs, or pigs. The animal model may also be used to determine the appropriate concentration range and route of administration. Such information can then be used to determine useful doses and routes for administration in humans. In calculating the Human Equivalent Dose (HED) it is recommended to use the conversion table provided in Guidance for Industry and Reviewers document (2002, U.S. Food and Drug Administration, Rockville, Md., USA).

Generally, an effective dose will be from 0.01 mg/kg to 100 mg/kg, preferably 0.05 mg/kg to 50 mg/kg. For any compound, the therapeutically effective dose can be estimated initially either in cell culture assays or in animal models, usually mice, rats, guinea pigs, rabbits, dogs, or pigs. The precise effective dose for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician.

Compositions may be administered individually to a patient or may be administered in combination with other agents, drugs or hormones.

The medicament may also contain a pharmaceutically acceptable carrier, for administration of a therapeutic agent. Such carriers include antibodies and other polypeptides, genes and other therapeutic agents such as liposomes, provided that the carrier does not induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The medicament of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal or rectal means.

The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include refilled, pre-measured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form. Dosage treatment may be a single dose schedule or a multiple dose schedule.

As above disclosed, the compounds of the present invention are useful as medicaments due to their Hsp90 inhibiting properties for the treatment of disorders where such inhibition result in improving the health of the patient. In particular, patients suffering from cancer diseases, neurodegenerative diseases, inflammatory diseases, cerebral ischemia and malaria can be treated. Objects of the present invention are pharmaceutical compositions containing one or more of the compounds of formula (I) described earlier, in combination with excipients and/or pharmacologically acceptable diluents.

The compositions in question may, together with the compounds of formula (I), contain known active principles.

A further object of the invention is a process for the preparation of pharmaceutical compositions characterised by mixing one or more compounds of formula (I) with suitable excipients, stabilizers and/or pharmaceutically acceptable diluents.

An embodiment of this invention is that of compounds of formula (I) described earlier, wherein $R^4$ represents NHC(D)ER$^4$ with D being 0 and E being absent, or NR$^5$R$^6$.

Another embodiment of this invention is that of compounds of formula (I) described earlier, wherein X represents alkyl or halogen.

A still another embodiment of the present invention consists of the compounds selected from the group consisting of 4-acetylamino-5-(5-chloro-2,4-dihydroxy-phenyl)-isoxazole-3-carboxylic acid ethylamide SST0072AA1; 5-(5-chloro-2,4-dihydroxy-phenyl)-4-(4-methoxy-benzoylamino)-isoxazole-3-carboxylic acid ethylamide SST0081AA1; 5-(5-chloro-2,4-dihydroxy-phenyl)-4-(3,4-dimethoxy-benzoylamino)-isoxazole-3-carboxylic acid ethylamide SST0100AA1; 5-(5-chloro-2,4-dihydroxy-phenyl)-4-(3,4,5-trimethoxy-benzoylamino)-isoxazole-3-carboxylic acid ethylamide SST0101AA1; 5-(5-chloro-2,4-dihydroxy-phenyl)-4-(2,2-dimethyl-propionylamino)-isoxazole-3-carboxylic acid ethylamide SST0091AA1; 4-[(adamantane-1-carbonyl)-amino]-5-(5-chloro-2,4-dihydroxy-phenyl)-isoxazole-3-carboxylic acid ethylamide SST0093AA1; 4-acryloylamino-5-(5-chloro-2,4-dihydroxy-phenyl)-isoxazole-3-carboxylic acid ethylamide SST0098AA1; 5-(5-chloro-2,4-dihydroxy-phenyl)-4-[(3-methyl-thiophene-2-carbonyl)-amino]-isoxazole-3-carboxylic acid ethylamide SST0092AA1; 5-(5-chloro-2,4-dihydroxy-phenyl)-4-(3-morpholin-4-yl-propionylamino)-isoxazole-3-carboxylic acid ethylamide SST0099AA1; 4-(4-bromo-benzoylamino)-5-(5-chloro-2,4-dihydroxy-phenyl)-isoxazole-3-carboxylic acid ethylamide SST0102AA1; 5-(2,4-dihydroxy-5-isopropyl-phenyl)-4-(4-methoxy-benzoylamino)-isoxazole-3-carboxylic acid ethylamide SST0107AA1; 4-acetylamino-5-(2,4-dihydroxy-5-isopropyl-phenyl)-isoxazole-3-carboxylic acid ethylamide SST0113AA1; 5-(2,4-dihydroxy-5-isopropyl-phenyl)-4-(2,2-dimethyl-propionylamino)-isoxazole-3-carboxylic acid ethylamide SST0114AA1; 5-(2,4-dihydroxy-5-isopropyl-phenyl)-4-[(3-methyl-thiophene-2-carbonyl)-amino]-isoxazole-3-carboxylic acid ethylamide SST0115AA1; 5-(2,4-dihydroxy-5-isopropyl-phenyl)-4-(3-morpholin-4-yl-propionylamino)-isoxazole-3-carboxylic acid ethylamide SST0116AA1; 4-(3-(4-methylpiperazin-1-yl)propanamido)-N-ethyl-5-(2,4-dihydroxy-5-isopropylphenyl)-isoxazole-3-carboxamide SST0203AA1; 1H-indole-6-carboxylic acid [5-(2,4-dihydroxy-5-isopropyl-phenyl)-3-ethyl carbamoyl-isoxazol-4-yl]-amide SST0220AA1; 5-(2,4-dihydroxy-5-isopropyl-phenyl)-4-(4-morpholin-4-yl-methyl-benzoyl amino)-isoxazole-3-carboxylic acid ethylamide hydrochloride SST0201CL1; 4-(cyclohexanecarbonyl-amino)-5-(2,4-dihydroxy-5-isopropyl-phenyl)-isoxazole-3-carboxylic acid ethylamide SST0221AA1; 5-(2,4-dihydroxy-5-isopropyl-phenyl)-4-[(trans-4-pentyl-cyclohexanecarbonyl)-amino]-isoxazole-3-carboxylic acid ethylamide SST0222AA1; 5-(2,4-dihydroxy-5-isopropyl-phenyl)-4-[(4-trifluoromethyl-cyclohexane carbonyl)-amino]-isoxazole-3-carboxylic acid ethylamide SST0223AA1; N$^5$-(3-(ethylcarbamoyl)-5-(2,4-dihydroxy-5-isopropylphenyl)-isoxazol-4-yl)-N$^3$-ethylisoxazole-3,5-dicarboxamide SST0211AA1; 5-(2,4-dihydroxy-5-isopropyl-phenyl)-4-[(4-methoxy-cyclohexanecarbonyl)-amino]-isoxazole-3-carboxylic acid ethylamide SST0226AA1; 4-[(4-tert-butyl-cyclohexanecarbonyl)-amino]-5-(2,4-dihydroxy-5-isopropyl-phenyl)-isoxazole-3-carboxylic acid ethylamide SST0227AA1; 4-[(4-amino-cyclohexanecarbonyl)-amino]-5-(2,4-dihydroxy-5-isopropyl-phenyl)-isoxazole-3-carboxylic acid ethylamide SST0228CL1; 4-[(4-aminomethyl-cyclohexanecarbonyl)-amino]-5-(2,4-dihydroxy-5-isopropyl-phenyl)-isoxazole-3-carboxylic acid ethylamide SST0229CL1; 4-(4-methoxybenzylamino)-5-(5-chloro-2,4-dihydroxyphenyl)-N-ethylisoxazole-3-carboxamide SST0207AA1; 4-((3-methylthiophen-2-yl)methylamino)-5-(5-chloro-2,4-dihydroxyphenyl)-N-ethylisoxazole-3-carboxamide SST0206AA1; 5-(5-chloro-2,4-dihydroxyphenyl)-4-(cyclohexylamino)-N-ethylisoxazole-3-carboxamide SST0208AA1; 4-(1-methylpiperidin-4-ylamino)-5-(5-chloro-2,4-dihydroxyphenyl)-N-ethylisoxazole-3-carboxamide SST0209AA1; Methyl 5-((3-(ethylcarbamoyl)-5-(5-chloro-2,4-dihydroxyphenyl)isoxazol-4-ylamino)methyl) isoxazole-3-carboxylate SST0210AA1; 4-((3-(hydroxymethyl)isoxazol-5-yl)methylamino)-5-(5-chloro-2,4-dihydroxyphenyl)-N-ethylisoxazole-3-carboxamide SST0212AA1; 4-(4-methoxybenzamido)-5-(5-chloro-2,4-dihydroxyphenyl)-N-(2,2,2-trifluoroethyl)-isoxazole-3-carboxamide SST0204AA1; 4-(4-methoxybenzamido)-5-(5-chloro-2,4-dihydroxyphenyl)-isoxazol-3-yl-(3,3-difluoroazetidin-1yl)-methanone SST0205AA1; 5-(5-chloro-2,4-dihydroxy-phenyl)-4-(4-methoxy-benzoylamino)-isoxazol-3-yl-(4-methylpiperazin-1-yl)-methanone SST0123AA1; 5-(2,4-dihydroxy-5-isopropyl-phenyl)-4-(3,4-dimethoxy-benzoylamino)-isoxazole-3-carboxylic acid ethylamide; 5-(2,4-dihydroxy-5-isopropyl-phenyl)-4-(3,4,5-trimethoxy-benzoylamino)-isoxazole-3-carboxylic acid ethylamide; 4-[(adamantane-1-carbonyl)-amino]-5-(2,4-dihydroxy-5-isopropyl-phenyl)-isoxazole-3-carboxylic acid ethylamide; 4-acryloylamino-5-(2,4-dihydroxy-5-isopropyl-phenyl)-isoxazole-3-carboxylic acid ethylamide; 4-(4-bromo-benzoylamino)-5-(2,4-dihydroxy-5-isopropyl-phenyl)-isoxazole-3-carboxylic acid ethylamide; 5-(2,4-dihydroxy-5-isopropyl-phenyl)-4-(4-methoxy-benzenesulfonylamino)-isoxazole-3-carboxylic acid ethylamide; 4-amino-5-(2,4-dihydroxy-5-isopropyl-phenyl)-isoxazole-3-carboxylic acid ethylamide; 5-(2,4-dihydroxy-5-isopropyl-phenyl)-4-(toluene-4-sulfonylamino)]-isoxazole-3-carboxylic acid ethylamide and 5-(2,4- dihydroxy-5-isopropyl-phenyl)-4-[bis-(toluene-4-sulfonylamino)]-isoxazole-3-carboxylic acid ethylamide.

Preferred compounds are selected from the group consisting of 4-acetylamino-5-(5-chloro-2,4-dihydroxy-phenyl)-isoxazole-3-carboxylic acid ethylamide SST0072AA1; 5-(5-chloro-2,4-dihydroxy-phenyl)-4-(4-methoxy-benzoylamino)-isoxazole-3-carboxylic acid ethylamide SST0081AA1; 5-(5-chloro-2,4-dihydroxy-phenyl)-4-(3,4-dimethoxy-benzoylamino)-isoxazole-3-carboxylic acid ethylamide SST0100AA1; 5-(5-chloro-2,4-dihydroxy-phenyl)-4-(3,4,5-trimethoxy-benzoylamino)-isoxazole-3-carboxylic acid ethylamide SST0101AA1; 5-(5-chloro-2,4-dihydroxy-phenyl)-4-(2,2-dimethyl-propionylamino)-isoxazole-3-carboxylic acid ethylamide SST0091AA1; 4-[(adamantane-1-carbonyl)-amino]-5-(5-chloro-2,4-dihydroxy-phenyl)-isoxazole-3-carboxylic acid ethylamide SST0093AA1; 4-acryloylamino-5-(5-chloro-2,4-dihydroxy-phenyl)-isoxazole-3-carboxylic acid ethylamide SST0098AA1; 5-(5-chloro-2,4-dihydroxy-phenyl)-4-[(3-methyl-thiophene-2-carbonyl)-amino]-isoxazole-3-carboxylic acid ethylamide SST0092AA1; 5-(5-chloro-2,4-dihydroxy-phenyl)-4-(3-morpholin-4-yl-propionylamino)-isoxazole-3-carboxylic acid ethylamide SST0099AA1; 4-(4-bromo-benzoylamino)-5-(5-chloro-2,4-dihydroxy-phenyl)-isoxazole-3-carboxylic acid ethylamide SST0102AA1; 5-(2,4-dihydroxy-5-isopropyl-phenyl)-4-(4-methoxy-benzoylamino)-isoxazole-3-carboxylic acid ethylamide SST0107AA1; 4-acetylamino-5-(2,4-dihydroxy-5-isopropyl-phenyl)-isoxazole-3-carboxylic acid ethylamide SST0113AA1; 5-(2,4-dihydroxy-5-isopropyl-phenyl)-4-(2,2-dimethyl-propionylamino)-isoxazole-3-carboxylic acid ethylamide SST0114AA1; 5-(2,4-dihydroxy-5-isopropyl-phenyl)-4-[(3-methyl-thiophene-2-carbonyl)-amino]-isoxazole-3-carboxylic acid ethylamide SST0115AA1; 5-(2,4-dihydroxy-5-isopropyl-phenyl)-4-(3-morpholin-4-yl-propionylamino)-isoxazole-3-carboxylic acid ethylamide SST0116AA1; 4-(3-(4-methylpiperazin-1-yl)propanamido)-N-ethyl-5-(2,4-dihydroxy-5-isopropylphenyl)-isoxazole-3-carboxamide SST0203AA1; 1H-indole-6-carboxylic acid [5-(2,4-dihydroxy-5-isopropyl-phenyl)-3-ethyl carbamoyl-isoxazol-4-yl]-amide SST0220AA1; 5-(2,4-dihydroxy-5-isopropyl-phenyl)-4-(4-morpholin-4-yl-methyl-benzoyl amino)-isoxazole-3-carboxylic acid ethylamide hydrochloride SST0201CL1; 4-(cyclohexanecarbonyl-amino)-5-(2,4-dihydroxy-5-isopropyl-phenyl)-isoxazole-3-carboxylic acid ethylamide SST0221AA1; 5-(2,4-dihydroxy-5-isopropyl-phenyl)-4-[(trans-4-pentyl-cyclohexanecarbonyl)-amino]-isoxazole-3-carboxylic acid ethylamide SST0222AA1; 5-(2,4-dihydroxy-5-isopropyl-phenyl)-4-[(4-trifluoromethyl-cyclohexane carbonyl)-amino]-isoxazole-3-carboxylic acid ethylamide SST0223AA1; $N^5$-(3-(ethylcarbamoyl)-5-(2,4-dihydroxy-5-isopropylphenyl)-isoxazol-4-yl)-$N^3$-ethylisoxazole-3,5-dicarboxamide SST0211AA1; 5-(2,4-dihydroxy-5-isopropyl-phenyl)-4-[(4-methoxy-cyclohexanecarbonyl)-amino]-isoxazole-3-carboxylic acid ethylamide SST0226AA1; 4-[(4-tert-butyl-cyclohexanecarbonyl)-amino]-5-(2,4-dihydroxy-5-isopropyl-phenyl)-isoxazole-3-carboxylic acid ethylamide SST0227AA1; 4-[(4-amino-cyclohexanecarbonyl)-amino]-5-(2,4-dihydroxy-5-isopropyl-phenyl)-isoxazole-3-carboxylic acid ethylamide SST0228CL1; 4-[(4-aminomethyl-cyclohexanecarbonyl)-amino]-5-(2,4-dihydroxy-5-isopropyl-phenyl)-isoxazole-3-carboxylic acid ethylamide SST0229CL1; 4-(4-methoxybenzylamino)-5-(5-chloro-2,4-dihydroxyphenyl)-N-ethylisoxazole-3-carboxamide SST0207AA1; 4-((3-methylthiophen-2-yl)methylamino)-5-(5-chloro-2,4-dihydroxyphenyl)-N-ethylisoxazole-3-carboxamide SST0206AA1; 5-(5-chloro-2,4-dihydroxyphenyl)-4-(cyclohexylamino)-N-ethylisoxazole-3-carboxamide SST0208AA1; 4-(1-methylpiperidin-4-ylamino)-5-(5-chloro-2,4-dihydroxyphenyl)-N-ethylisoxazole-3-carboxamide SST0209AA1; Methyl 5-((3-(ethylcarbamoyl)-5-(5-chloro-2,4-dihydroxyphenyl)isoxazol-4-ylamino)methyl) isoxazole-3-carboxylate SST0210AA1; 4-((3-(hydroxymethyl)isoxazol-5-yl)methylamino)-5-(5-chloro-2,4-dihydroxyphenyl)-N-ethylisoxazole-3-carboxamide SST0212AA1; 4-(4-methoxybenzamido)-5-(5-chloro-2,4-dihydroxyphenyl)-N-(2,2,2-trifluoroethyl)-isoxazole-3-carboxamide SST0204AA1; 4-(4-methoxybenzamido)-5-(5-chloro-2,4-dihydroxyphenyl)-isoxazol-3-yl-(3,3-difluoroazetidin-1yl)-methanone SST0205AA1 and 5-(5-chloro-2,4-dihydroxy-phenyl)-4-(4-methoxy-benzoylamino)-isoxazol-3-yl-(4-methylpiperazin-1-yl)-methanone SST0123AA1. Even more preferred compounds are selected from the group consisting of 5-(5-chloro-2,4-dihydroxy-phenyl)-4-(2,2-dimethyl-propionylamino)-isoxazole-3-carboxylic acid ethylamide SST0091AA1, 4-[(adamantane-1-carbonyl)-amino]-5-(5-chloro-2,4-dihydroxy-phenyl)-isoxazole-3-carboxylic acid ethylamide SST0093AA1, 5-(5-chloro-2,4-dihydroxy-phenyl)-4-[(3-methyl-thiophene-2-carbonyl)-amino]-isoxazole-3-carboxylic acid ethylamide SST0092AA1, 5-(5-chloro-2,4-dihydroxy-phenyl)-4-(3-morpholin-4-yl-propionylamino)-isoxazole-3-carboxylic acid ethylamide SST0099AA1, 4-acetylamino-5-(2,4-dihydroxy-5-isopropyl-phenyl)-isoxazole-3-carboxylic acid ethylamide SST0113AA1, 5-(2,4-dihydroxy-5-isopropyl-phenyl)-4-(2,2-dimethyl-propionylamino)-isoxazole-3-carboxylic acid ethylamide SST0114AA1 and 5-(2,4-dihydroxy-5-isopropyl-phenyl)-4-[(3-methyl-thiophene-2-carbonyl)-amino]-isoxazole-3-carboxylic acid ethylamide SST0115AA1.

The following illustrated examples are by no means an exhaustive list of what the present invention intends to protect.

EXAMPLES

Abbreviations $Ac_2O$: acetic anhydride
AcOEt: ethyl acetate
$BF_3.OEt_2$: boron trifluoride dietherate
Boc: t-butoxycarbonyl
DCM: dichloromethane
DIPEA: diisopropylethylamine
DMF: dimethylformamide
MeOH: methanol
EtOH: ethanol
$Et_2O$: diethyl ether
RP-HPLC: reversed phase-high-performance liquid chromatography
RT: room temperature
Rt: retention time
Tf: triflate
TEA: triethylamine
TFA: trifluoroacetic acid General Remarks: Reaction courses and product mixtures were routinely monitored by thin-layer chromatography (TLC) on silica gel $F_{254}$ Merck plates. Flash column chromatography was carried out using silica gel (Merck 230-400 mesh). Nuclear magnetic resonance ($^1H$ and $^{13}C$ NMR) spectra were gathered, with a Bruker AC-200 spectrometer or with a Varian Mercury Plus 300 or 400, and chemical shifts are given in part per million (ppm) downfield from tetramethylsilane as internal standard. The coupling constants are given in Hz. Mass spectra were obtained with an ESI MICROMASS ZMD2000.

All drying operations were performed over anhydrous sodium sulphate. Flash column chromatography (medium pressure) was carried out using silica gel (Merck 230-400 mesh).

Examples 1 has been synthesized following the procedure as described in scheme 1.

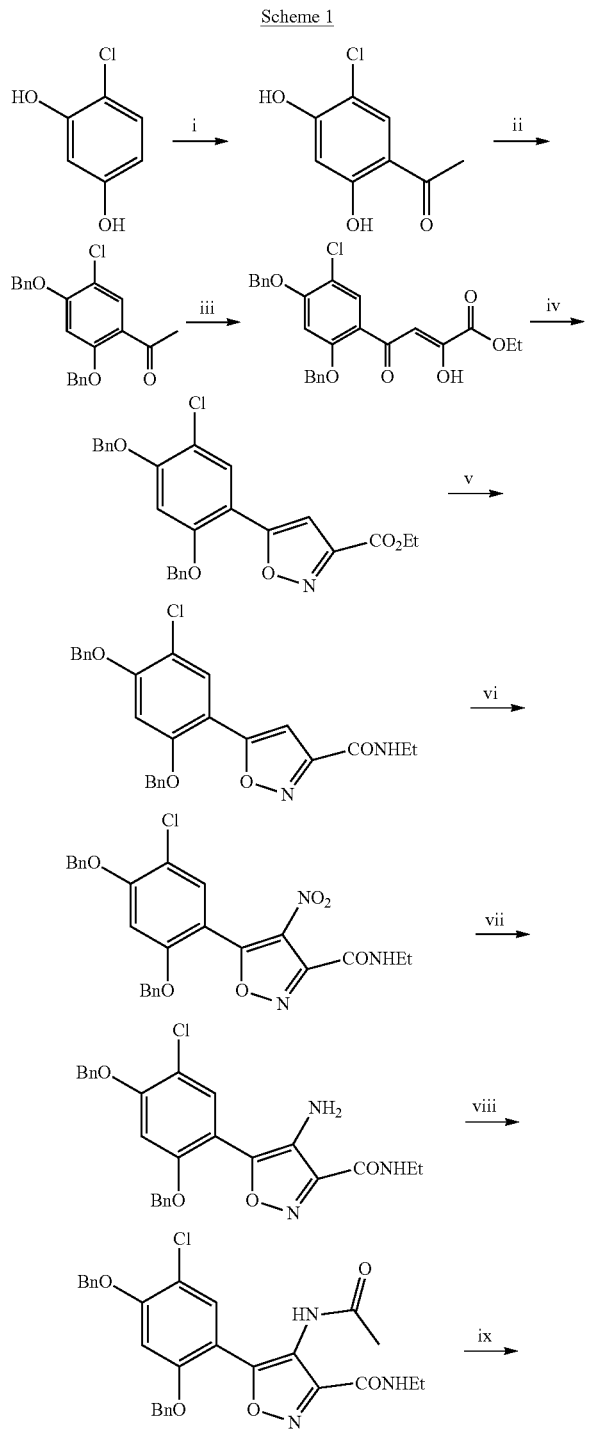

i: AcOH, BF$_3$.OEt, 90° C.; ii: BnBr, K$_2$CO$_3$, AcCN; iii: OHCCO$_2$Et, Na/EtOH; iv: NH$_2$OH, EtOH; v: EtNH$_2$, MeOH, EtOH; vi: HNO$_3$, Ac$_2$O; vii: H$_2$O, THF, NH$_4$Cl, Zn; viii: AcCl, NEt$_3$, DCM; ix: BCl$_3$, DCM Example 1

4-acetylamino-5-(5-chloro-2,4-dihydroxy-phenyl)-isoxazole-3-carboxylic acid ethylamide SST0072AA1

Step i: 1-(5-chloro-2,4-dihydroxyphenyl)-ethanone

Acetic acid (17.5 ml) was added dropwise to a suspension of 4-chlorobenzene-1,3-diol (20 g, 0.138 mol) in BF$_3$.OEt$_2$ (100 ml) under a nitrogen atmosphere. The reaction mixture was stirred at 90° C. for 3.5 h and then allowed to cool to RT, causing a solid to precipitate. The mixture was poured into a 10% w/v aqueous sodium acetate solution (350 ml). This mixture was then stirred vigorously for 2.5 h to afford a light brown solid, which was filtered, washed with water, and air-dried overnight to afford the title compound 1-(5-chloro-2,4-dihydroxyphenyl)-ethanone (11.3 g, 44%).

$^1$H NMR (200 MHz CDCl$_3$), δ: 2.56 (s, 3H), 6.11 (s, 1H), 6.59 (s, 1H), 7.70 (s, 1H), 12.48 (s, 1H).

Step ii: 1-[2,4-bis(benzyloxy)-5-chlorophenyl]ethanone

Benzyl bromide (17.5 ml, 0.147 mol) was added to a mixture of 1-(5-chloro-2,4-dihydroxyphenyl)ethanone (11 g, 0.059 mol) and potassium carbonate (20.34 g, 0.147 mol) in acetonitrile (180 ml). The mixture was stirred at reflux for 6 h and then allowed to cool to RT and stirred overnight. The mixture was filtered, and the solid residue was rinsed with DCM (3×50 ml). The combined organic filtrates were evaporated under vacuo to give a pale yellow solid. The latter was triturated with a mixture of hexane/EtOAc (175/7.5) and filtered to afford the title compound 1-[2,4-bis(benzyloxy)-5-chlorophenyl]ethanone (20.4 g, 93% yield) as an off-white solid.

$^1$H NMR (200 MHz CDCl$_3$), δ: 2.54 (s, 3H), 5.07 (s, 2H), 5.15 (s, 2H), 6.55 (s, 1H), 7.36-7.42 (m, 10H), 7.91 (s, 1H).

Step iii: ethyl 4-(2,4-bis(benzyloxy)-5-chlorophenyl)-2-hydroxy-4-oxobut-2-enoate Sodium metal (1.35 g, 58 mmol) was cut into small pieces, rinsed with hexane to remove mineral oil, and added portion wise to anhydrous EtOH (100 ml) under a nitrogen atmosphere over a period of 20 min. The reaction mixture was stirred for a further 10 min until all sodium had reacted. 1-[2,4-bis(benzyloxy)-5-chlorophenyl]ethanone (10 g, 27.3 mmol) was added portion wise over 5 min, and the resulting suspension was then stirred for further 5 min at RT. Diethyloxalate (6 ml, 43 mmol) was added, resulting in a thick yellow coloured precipitate. The reaction mixture was heated to reflux for 4 h, affording a dark homogeneous solution, which, upon cooling, produced a solid mass to which acetic acid (6 ml) was added. The mixture was triturated to afford a yellow solid, which was filtered, washed sequentially with water, EtOH, and Et$_2$O, and then dried under vacuo to afford the title compound ethyl 4-(2,4-bis(benzyloxy)-5-chlorophenyl)-2-hydroxy-4-oxobut-2-enoate (12.4 g, 98%) as a yellow solid.

$^1$H NMR (200 MHz CDCl$_3$), δ: 1.28 (t, J=7.4 Hz, 3H), 4.28 (q, J=7.4 Hz, 2H), 5.11 (s, 2H), 5.18 (s, 2H), 6.58 (s, 1H), 7.35-7.40 (m, 10H), 8.02 (s, 1H). 15.36 (br, 1H).

Step iv: ethyl 5-(2,4-bis(benzyloxy)-5-chlorophenyl)isoxazole-3-carboxylate

Hydroxylamine hydrochloride (0.89 g, 12.8 mmol) was added to a suspension of 4-(2,4-bis(benzyloxy)-5-chlorophenyl)-2-hydroxy-4-oxobut-2-enoate (5.0 g, 10.7 mmol) in EtOH (100 ml). The reaction mixture was heated to reflux for 3.5 h and then allowed to cool to RT. The resulting suspension was filtered, washed sequentially with EtOH (2×10 ml), water (2×10 ml), and EtOH (2×10 ml), and dried under vacuo to afford the title compound ethyl 5-(2,4-bis(benzyloxy)-5-chlorophenyl)isoxazole-3-carboxylate (3.97 g, 80%) as a flocculent light-yellow solid.

$^1$H NMR (200 MHz CDCl$_3$), δ: 1.40 (t, J=7.2 Hz, 3H), 4.41 (q, J=7.2 Hz, 2H), 5.14 (s, 4H), 6.61 (s, 1H), 7.01 (s, 1H), 7.38 (s, 10H), 8.0 (s, 1H).

[M+H]$^+$ 464.4/465.9

Step v: 5-(2,4-bis-benzyloxy-5-chloro-phenyl)-isoxazole-3-carboxylic acid ethylamide Ethylamine in MeOH solution (2 M, 80 mmol, 40 ml) was added to a suspension of ethyl 5-(2,4-bis(benzyloxy)-5-chlorophenyl)isoxazole-3-carboxylate (9.51 mmol) in EtOH (50 ml) and the reaction mixture was heated to 80° C. with stirring for 18 h, affording a yellow homogeneous solution, which was allowed to cool to RT. A flocculent colourless solid formed upon cooling to 4° C. After filtration, washing with cold EtOH and drying under vacuo, the desired compound was obtained.

$^1$H NMR (200 MHz CDCl$_3$), δ: 1.25 (t, J=7.2 Hz, 3H), 3.41-3.57 (m, 2H), 5.10 (s, 2H), 5.16 (s, 2H), 6.59 (s, 1H), 6.80 (br, 1H), 7.09 (s, 10H), 7.35-7.40 (m, 10H), 7.97 (s, 1H).

[M+H]$^+$ 463.4/464.8

Step vi: 5-(2,4-bis-benzyloxy-5-chloro-phenyl)-4-nitro-isoxazole-3-carboxylic acid ethylamide A suspension of 5-(2,4-bis(benzyloxy)-5-chloro-phenyl)-isoxazole-3-carboxylic acid ethylamide (1 g, 2.2 mmol) in Ac$_2$O (20 ml) was cooled to 0° C. and HNO$_3$ (0.26 ml, 4.3 mmol) was added dropwise under stirring, the temperature being maintained between 0-5° C. After the addition was complete, the mixture was stirred for 70 h at 5-10° C. and then poured into ice and extracted with DCM (3×40 ml). The extract was dried and concentrated under vacuo. The yellow solid obtained was triturated with Et$_2$O and filtered to give 5-[2,4-bis(benzyloxy)-5-chlorophenyl]-N-ethyl-4-nitroisoxazole-3-carboxamide (810 mg, 73%).

$^1$H NMR (200 MHz CDCl$_3$), δ: 1.26 (t, J=7.4 Hz, 3H), 3.46-3.55 (m, 2H), 5.0 (s, 2H), 5.10 (s, 2H), 6.57 m 2H, 7.23-7.29 (m, 2H), 7.32-7.37 (m, 8H), 7.66 (s, 1H).

Step vii: 4-amino-5-(2,4-bis-benzyloxy-5-chloro-phenyl)-isoxazole-3-carboxylic acid ethylamide A solution of 5-(2,4-bis-benzyloxy-5-chloro-phenyl)-4-nitro-isoxazole-3-carboxylic acid ethylamide (1 g, 1.97 mmol) in THF (7 ml) was added to a solution of NH$_4$Cl (2.7 g, 50 mmol) in water (15 ml). Zinc dust (4 g, 61 mmol) was then added portion wise over 15 min with stirring at 0° C. After 30 min at 0° C., the mixture was filtered and the resulting cake was rinsed with MeOH. The combined filtrate were evaporated under vacuo to give 5-[2,4-bis(benzyloxy)-5-chlorophenyl]-4-amino-N-ethylisoxazole-3-carboxamide (820 mg, 82%).

$^1$H NMR (200 MHz CDCl$_3$), δ: 1.24 (t, J=7.2 Hz, 3H), 3.38-3.53 (m, 2H), 5.02 (s, 2H), 5.15 (s, 2H), 6.64 (s, 1H), 6.79 (br, 1H), 7.35-7.42 (m, 10H), 7.64 (s, 1H).

[M+H]$^+$ 478.3/479.4

Step viii: 4-acetylamino-5-(2,4-bis-benzyloxy-5-chloro-phenyl)-isoxazole-3-carboxylic acid ethylamide To a solution of acetyl chloride (1.45 mmol) in DCM were added 5-[2,4-bis(benzyloxy)-5-chlorophenyl]-4-amino-N-ethylisoxazole-3-carboxamide (1.45 mmol, 700 mg) and TEA (1.74 mmol, 0.24 ml) dropwise. The mixture was stirred for 5 h, diluted with DCM and washed HCl 1N. The organic extract was dried and filtered. Solvents were removed under vacuo to give the crude residue that was purified by flash chromatography on silica gel.

$^1$H NMR (200 MHz CDCl$_3$), δ: 1.28 (t, J=7.4 Hz, 3H), 1.81 (s, 3H), 3.43-3.52 (m, 2H), 4.99 (s, 2H), 5.14 (s, 2H), 6.61 (s, 1H), 6.86 (br, 1H), 7.27-7.45 (m, 10H), 7.66 (s, 1H), 7.75 (s, 1H), 8.40 (s, 1H).

Step ix: 4-acetylamino-5-(5-chloro-2,4-dihydroxy-phenyl)-isoxazole-3-carboxylic acid ethylamide A solution of 4-acetylamino-5-(2,4-bis-benzyloxy-5-chloro-phenyl)-isoxazole-3-carboxylic acid ethylamide (0.35 mmol) in DCM (10 ml) under inert atmosphere was cooled at 0° C. and BCl$_3$ in DCM (1M, 1.05 mmol, 1.05 ml) was added dropwise. The reaction was stirred at 0° C. for 20 min, the cooling bath was then removed and the mixture stirred for a further 50 min. The mixture was cooled back and then quenched by cautious addition of saturated aqueous NaHCO$_3$ solution (20 ml). The DCM was removed under vacuo and water (20 ml) was added. The mixture was then extracted with EtOAc (200 ml). The phases were separated and the organic phase was washed with water (2×30 ml), sat. aqueous NaCl solution (50 ml) and then dried and filtered. Solvent was removed under vacuo and the crude product purified by flash chromatography on silica gel.

$^1$H NMR (400 MHz CD$_3$OD), δ: 1.21 (t, J=6.8 Hz, 3H), 2.07 (s, 3H), 3.39 (q, J=6.8 Hz, 2H), 6.55 (s, 1H), 7.40 (s, 1H).

$^{13}$C NMR (100 MHz CD$_3$OD), δ: 14.7, 22.6, 35.3, 104.9, 108.2, 113.2, 114.2, 130.9, 156.3, 156.5, 157.6, 161.5, 162.7, 172.4.

[M+H]$^+$ 340.0/341.9

Examples 2 to 14 were synthesized following procedures described in step viii and ix of example 1 using the appropriate acid chloride derivative for the amide formation (i.e., step viii).

Example 2

5-(5-chloro-2,4-dihydroxy-phenyl)-4-(4-methoxy-benzoylamino)-isoxazole-3-carboxylic acid ethylamide SST0081AA1

Step viii: 5-(2,4-bis-benzyloxy-5-chloro-phenyl)-4-(4-methoxy-benzoylamino)-isoxazole-3-carboxylic acid ethylamide $^1$H NMR (200 MHz CDCl$_3$), δ: 1.28 (t, J=7.2 Hz, 3H), 3.45-3.54 (m, 2H), 3.84 (s, 3H), 4.85 (s, 2H), 5.11 (s, 2H), 6.57 (s, 1H), 6.83 (d, J=9.0 Hz, 2H), 6.95 (br, 1H), 7.08-7.13 (m, 2H), 7.21-7.29 (m, 2H), 7.35-7.43 (m, 6H), 7.55 (d, J=9.0 Hz, 2H), 7.75 (s, 1H), 9.47 (s, 1H).
[M+H]+ 612.1/613.3

Step ix: 5-(5-chloro-2,4-dihydroxy-phenyl)-4-(4-methoxy-benzoylamino)-isoxazole-3-carboxylic acid ethylamide $^1$H NMR (400 MHz DMSO), δ: 1.06 (t, J=6.8 Hz, 3H), 3.19-3.24 (m, 3H), 3.82 (s, 3H), 6.64 (s, 1H), 7.04 (d, J=8.8 Hz, 2H), 7.43 (s, 1H), 7.87 (d, J=8.8 Hz, 2H), 8.71 (t, J=5.6 Hz, 1H), 9.62 (s, 1H), 10.48 (br, 1H), 10.68 (s, 1H).
$^{13}$C NMR (100 MHz DMSO), δ: 14.4, 33.5, 55.3, 103.8, 106.2, 110.4, 113.6, 125.7, 129.4, 155.3, 155.5, 155.7, 158.5, 161.3, 162.0, 164.9. [M+H]+ 432.1/434.1

Example 3

5-(5-chloro-2,4-dihydroxy-phenyl)-4-(3,4-dimethoxy-benzoylamino)-isoxazole-3-carboxylic acid ethylamide SST0100AA1

Step viii: 5-(2,4-bis-benzyloxy-5-chloro-phenyl)-4-(3,4-dimethoxy-benzoylamino)-isoxazole-3-carboxylic acid ethylamide $^1$H NMR (200 MHz CDCl$_3$), δ: 1.27 (t, J=7.2 Hz, 3H), 3.46-3.54 (m, 2H), 3.84 (s, 3H), 3.92 (s, 3H), 4.85 (s, 2H), 5.10 (s, 2H), 6.57 (s, 1H), 6.74 (d, J=8.6 Hz, 1H), 6.94 (br, 1H), 7.05-7.12 (m, 2H), 7.22-7.25 (m, 2H), 7.32-7.40 (m, 8H), 7.75 (s, 1H), 9.56 (s 1H).

Step ix: 5-(5-chloro-2,4-dihydroxy-phenyl)-4-(3,4-dimethoxy-benzoylamino)-isoxazole-3-carboxylic acid ethylamide $^1$H NMR (400 MHz, DMSO), δ: 1.06 (t, J=6.8 Hz, 3H), 3.18-3.22 (m, 3H), 3.79 (s, 3H), 3.81 (s, 3H), 6.63 (s, 1H), 7.05 (d, J=8.8 Hz, 1H), 7.41 (s, 1H), 7.43 (d, J=1.6 Hz, 1H), 7.52 (dd, J=8.8, J=1.6 Hz, 1H), 8.69 (t, J=6.0 Hz, 1H), 9.59 (s, 1H), 10.44 (br, 1H), 10.66 (s, 1H).
$^{13}$C NMR (100 MHz, DMSO), δ: 14.4, 33.5, 55.5, 55.6, 103.8, 106.2, 110.7, 110.9, 113.6, 120.9, 125.7, 129.5, 148.2, 151.7, 155.6, 155.7, 158.5, 161.4, 165.0.
[M+H]+ 462.4/463.5.

Example 4

5-(5-chloro-2,4-dihydroxy-phenyl)-4-(3,4,5-trimethoxy-benzoylamino)-isoxazole-3-carboxylic acid ethylamide SST0101AA1

Step viii: 5-(2,4-bis-benzyloxy-5-chloro-phenyl)-4-(3,4,5-trimethoxy-benzoylamino)-isoxazole-3-carboxylic acid ethylamide $^1$H NMR (200 MHz CDCl$_3$), δ: 1.28 (t, J=7.2 Hz, 3H), 3.45-3.56 (m, 2H), 3.79 (s, 6H), 3.87 (s, 3H), 4.90 (s, 2H), 5.12 (s, 2H), 6.60 (s, 1H), 6.89 (s, 2H), 6.96 (br, 1H), 7.08-7.14 (m, 2H), 7.22-7.26 (m, 4H), 7.35-7.41 (m, 4H), 7.76 (s, 1H), 9.60 (s 1H).

Step ix: 5-(5-chloro-2,4-dihydroxy-phenyl)-4-(3,4,5-trimethoxy-benzoylamino)-isoxazole-3-carboxylic acid ethylamide $^1$H NMR (400 MHz, DMSO), δ: 1.08 (t, J=6.8 Hz, 3H), 3.19-3.23 (m, 2H), 3.71 (s, 3H), 3.83 (s, 6H), 6.64 (s, 1H), 7.23 (s, 2H), 7.43 (s, 1H), 8.72 (t, J=5.6 Hz 1H), 9.70 (br, 1H), 10.45 (s, 1H), 10.70 (s, 1H).
$^{13}$C NMR (100 MHz DMSO), δ: 14.4, 33.4, 33.5, 55.9, 60.0, 103.8, 105.1, 106.1, 113.4, 128.7, 129.4, 140.3, 152.6, 155.6, 155.8, 158.3, 161.5, 165.0.
[M+H]+ 492.4/494.4.

Example 5

5-(5-chloro-2,4-dihydroxy-phenyl)-4-(2,2-dimethyl-propionylamino)-isoxazole-3-carboxylic acid ethylamide SST0091AA1

Step viii: 5-(2,4-bis-benzyloxy-5-chloro-phenyl)-4-(2,2-dimethyl-propionylamino)-isoxazole-3-carboxylic acid ethylamide $^1$H NMR (400 MHz CDCl$_3$), δ: 1.82 (s, 9H), 1.29 (t, J=6.8 Hz, 3H), 3.49-3.53 (m, 2H), 4.98 (s, 2H), 5.13 (s, 2H), 6.59 (s, 1H), 6.91 (br, 1H), 7.24-7.26 (m, 2H), 7.31-7.43 (m, 8H), 7.62 (s, 1H), 9.01 (s, 1H).
[M+H]+ 562.5/563.7.

Step ix: 5-(5-chloro-2,4-dihydroxy-phenyl)-4-(2,2-dimethyl-propionylamino)-isoxazole-3-carboxylic acid ethylamide $^1$H NMR (400 MHz DMSO), δ: 1.06 (t, J=7.2 Hz, 3H), 1.14 (s, 9H), 3.19-3.24 (m, 2H), 6.66 (s, 1H), 7.34 (s, 1H), 8.58 (t, J=5.6 Hz, 1H), 8.83 (s, 1H), 10.50 (br, 1H), 10.70 (s, 1H).
$^{13}$C NMR (100 MHz DMSO), δ: 14.5, 27.1, 33.6, 38.3, 103.9, 106.2, 110.5, 113.5, 129.4, 155.2, 155.6, 155.7, 158.5, 161.2, 177.9.
[M+H]+ 382.2/384.2.

Example 6

4-[(adamantane-1-carbonyl)-amino]-5-(5-chloro-2,4-dihydroxy-phenyl)-isoxazole-3-carboxylic acid ethylamide SST0093AA1

Step viii: 4-[(adamantane-1-carbonyl)-amino]-5-(2,4-bis-benzyloxy-5-chloro-phenyl)-isoxazole-3-carboxylic acid ethylamide $^1$H NMR (200 MHz CDCl$_3$), δ: 1.30 (t, J=7.2 Hz, 3H), 1.58-1.70 (m, 12H), 1.94 (s, 3H), 3.46-3.60 (m, 2H), 4.98 (s, 2H), 5.16 (s, 2H), 6.61 (s, 1H), 6.92 (br, 1H), 7.30-7.44 (m, 10H), 7.64 (s, 1H), 8.99 (s, 1H).
[M+H]+ 640.4/641.4.

Step ix: 4-[(adamantane-1-carbonyl)-amino]-5-(5-chloro-2,4-dihydroxy-phenyl)-isoxazole-3-carboxylic acid ethylamide $^1$H NMR (400 MHz DMSO), δ: 1.09 (t, J=7.2 Hz, 3H), 1.65-1.69 (m, 6H), 1.81-1.82 (m, 6H), 1.99 (s, 3H), 3.18-3.24 (m, 2H), 6.67 (s, 1H), 7.34 (s, 1H), 8.74 (t, J=5.6 Hz, 1H), 10.55 (br, 2H).
$^{13}$C NMR (100 MHz DMSO), δ: 14.5, 33.3, 104.0, 107.8, 110.9, 124.4, 128.0, 148.9, 150.7, 153.4, 154.6, 160.3.
[M+H]+ 298.0/300.0.

Example 7

4-acryloylamino-5-(5-chloro-2,4-dihydroxy-phenyl)-isoxazole-3-carboxylic acid ethylamide SST0098AA1

Step viii: 4-acryloylamino-5-(2,4-bis-benzyloxy-5-chloro-phenyl)-isoxazole-3-carboxylic acid ethylamide $^1$H NMR (200 MHz CDCl$_3$), δ: 1.27 (t, J=7.0 Hz, 3H), 3.41-3.55 (m, 2H), 4.94 (s, 2H), 5.11 (s, 2H), 5.60 (dd, J=10.0, J=1.4 Hz, 1H), 5.94 (dd, J=16.8, J=10.0 Hz, 1H), 6.15 (dd, J=16.8, J=1.4 Hz, 1H), 6.58 (s, 1H), 6.90 (br, 1H), 7.31-7.41 (m, 10H), 7.69 (s, 1H), 8.76 (s, 1H).
[M+H]$^+$ 532.4/533.5.

Step ix: 4-acryloylamino-5-(5-chloro-2,4-dihydroxy-phenyl)-isoxazole-3-carboxylic acid ethylamide $^1$H NMR (400 MHz CD$_3$OD), δ: 1.22 (t, J=7.6 Hz, 3H), 3.23-3.41 (m, 2H), 5.76 (dd, J=10.4, J=1.6, 1H), 6.26 (dd, J=16.8, J=1.6, 1H), 6.39 (dd, J=16.8, J=10.4, 1H), 6.56 (s, 1H), 7.42 (s, 1H).
$^{13}$C NMR (100 MHz CD$_3$OD), δ: 14.7, 35.3, 104.9, 108.3, 111.6, 113.2, 128.2, 130.8, 131.5, 156.2, 157.6, 161.5, 162.6, 166.7.
[M+H]$^+$ 352.1/353.6.

Example 8

5-(5-chloro-2,4-dihydroxy-phenyl)-4-[(3-methyl-thiophene-2-carbonyl)-amino]-isoxazole-3-carboxylic acid ethylamide SST0092AA1

Step viii: 5-(2,4-bis-benzyloxy-5-chloro-phenyl)-4-[(3-methyl-thiophene-2-carbonyl)-amino]-isoxazole-3-carboxylic acid ethylamide $^1$H NMR (200 MHz CDCl$_3$), δ: 1.27 (t, J=7.0 Hz, 3H), 2.35 (s, 3H), 3.42-3.58 (m, 2H), 4.90 (s, 2H), 5.10 (s, 2H), 6.56 (s, 1H), 6.84 (d, J=4.8 Hz, 1H), 6.90 (br, 1H), 7.02-7.10 (m, 2H), 7.21-7.42 (m, 9H), 7.75 (s, 1H), 9.28 (s, 1H).
[M+H]$^+$ 602.3/603.4.

Step ix: 5-(5-chloro-2,4-dihydroxy-phenyl)-4-[(3-methyl-thiophene-2-carbonyl)-amino]-isoxazole-3-carboxylic acid ethylamide $^1$H NMR (400 MHz DMSO), δ: 1.09 (t, J=6.8 Hz, 3H), 2.43 (s, 3H), 3.20-3.25 (m, 2H), 6.65 (s, 1H), 7.01 (d, J=5.2 Hz, 1H), 7.44 (s, 1H), 7.66 (d, J=5.2 Hz, 1H), 8.58 (t, J=5.6 Hz, 1H), 9.29 (br, 1H), 10.70 (s, 2H).
$^{13}$C NMR (100 MHz DMSO), δ: 14.5, 15.3, 33.6, 103.9, 106.4, 113.4, 128.4, 129.3, 131.8, 141.2, 154.9, 155.9, 158.7, 160.6, 160.9.
[M+H]$^+$ 422.1/424.1.

Example 9

5-(5-chloro-2,4-dihydroxy-phenyl)-4-(3-morpholin-4-yl-propionylamino)-isoxazole-3-carboxylic acid ethylamide SST0099AA1

Step viii: 5-(2,4-bis-benzyloxy-5-chloro-phenyl)-4-(3-morpholin-4-yl-propionylamino)-isoxazole-3-carboxylic acid ethylamide A solution of 4-acryloylamino-5-(2,4-bis-benzyloxy-5-chloro-phenyl)-isoxazole-3-carboxylic acid ethylamide as described in example 7 (step viii), (170 mg, 0.32 mmol) and morpholine (1 ml) in EtOH (5 ml) was heated under reflux for 1 h.

Solvents were removed under reduced pressure, and the residue was chromatographed on silica gel (eluent: AcOEt/MeOH: 95/5).

$^1$H NMR (200 MHz CDCl$_3$), δ: 1.25 (t, J=7.4 Hz, 3H), 2.24-2.34 (m, 4H), 2.41-2.45 (m, 2H), 3.38-3.50 (m, 2H), 3.64-3.72 (m, 4H), 4.97 (s, 2H), 5.12 (s, 2H), 6.58 (s, 1H), 6.86 (br, 1H), 7.28-7.42 (m, 10H), 7.62 (s, 1H), 9.95 (m, 1H).
[M+H]$^+$ 619.6/621.5.

Step ix: 5-(5-chloro-2,4-dihydroxy-phenyl)-4-(3-morpholin-4-yl-propionylamino)-isoxazole-3-carboxylic acid ethylamide $^1$H NMR (400 MHz DMSO), δ: 1.09 (t, J=7.4 Hz, 3H), 2.36-2.40 (m, 4H), 2.51-2.55 (m, 4H), 3.19-3.25 (m, 2H), 3.33-3.39 (m, 2H), 3.49-3.54 (m, 2H), 6.73 (s, 1H), 7.29 (s, 1H), 8.65 (br, 1H), 10.09 (br, 1H), 10.81 (br, 1H).
$^{13}$C NMR (100 MHz DMSO), δ: 14.4, 32.5, 33.5, 52.8, 53.8, 65.9, 104.0, 106.2, 113.1, 129.3, 155.5, 158.5, 161.1, 170.5.
[M+H]$^+$ 439.4/440.5.

Example 10

4-(4-bromo-benzoylamino)-5-(5-chloro-2,4-dihydroxy-phenyl)-isoxazole-3-carboxylic acid ethylamide SST0102AA1

Step viii: 5-(2,4-bis-benzyloxy-5-chloro-phenyl)-4-(4-bromo-benzoylamino)-isoxazole-3-carboxylic acid ethylamide $^1$H NMR (200 MHz CDCl$_3$), δ: 1.29 (t, J=7.4 Hz, 3H), 3.47-3.52 (m, 2H), 4.85 (s, 2H), 5.15 (s, 2H), 6.60 (s, 1H), 6.88-7.00 (m, 1H), 7.08-7.11 (m, 2H), 7.24-7.29 (s, 2H), 7.34-7.44 (m, 10H), 7.78 (s, 1H), 9.52 (m, 1H).

Step ix: 4-(4-bromo-benzoylamino)-5-(5-chloro-2,4-dihydroxy-phenyl)-isoxazole-3-carboxylic acid ethylamide SST0102AA1

$^1$H NMR (200 MHz CD$_3$OD), δ: 1.22 (t, J=7.4 Hz, 3H), 3.33-3.41 (m, 2H), 6.54 (s, 1H), 7.49 (s, 1H), 7.67 (d, J=8.8 Hz, 2H), 7.80 (d, J=8.8 Hz, 2H), 10.81 (br, 1H).
$^{13}$C NMR (50 MHz CD$_3$OD), δ: 14.7, 35.4, 104.9, 108.4, 113.4, 114.3, 127.7, 130.4, 130.7, 132.8, 134.1, 156.1, 156.2, 157.6, 161.7, 162.4, 167.3.
[M+H]$^+$ 480.1/482.2/483.5.

Example 11 was synthesized following procedures described in scheme 1-steps vi-ix of example 1 starting from 5-(2,4-bis-benzyloxy-5-isopropyl-phenyl)-isoxazole-3-carboxylic acid ethylamide instead of 5-(2,4-bis-benzyloxy-5-chloro-phenyl)-isoxazole-3-carboxylic acid ethylamide and using the appropriate acid chloride derivative for the amide formation (i.e., step viii).

Example 11

5-(2,4-dihydroxy-5-isopropyl-phenyl)-4-(4-methoxy-benzoylamino)-isoxazole-3-carboxylic acid ethylamide SST0107AA1

Step vi: 5-(2,4-bis-benzyloxy-5-isopropyl-phenyl)-4-nitro-isoxazole-3-carboxylic acid ethylamide $^1$H NMR (200 MHz CDCl$_3$), δ: 1.22-1.26 (m, 9H), 3.24-3.38 (m, 1H), 3.43-3.57 (m, 2H), 5.02 (s, 4H), 6.54 (s, 1H), 6.59 (br, 1H), 7.30-7.39 (m, 10H), 7.46 (s, 1H).
[M+H]$^+$ 516.5.

Step vii: 4-amino-5-(2,4-bis-benzyloxy-5-isopropyl-phenyl)-isoxazole-3-carboxylic acid ethylamide $^1$H NMR (200 MHz CDCl$_3$), δ: 1.21-1.28 (m, 9H), 3.28-3.38 (m, 1H), 3.39-3.53 (m, 2H), 4.38 (br, 2H), 5.05 (s, 2H), 5.08 (s, 2H), 6.61 (s, 1H), 6.83 (br, 1H), 7.33-7.42 (m, 10H), 7.45 (s, 1H).
[M+H]$^+$ 486.6.

Step viii: 5-(2,4-bis-benzyloxy-5-isopropyl-phenyl)-4-(4-methoxy-benzoylamino)-isoxazole-3-carboxylic acid ethylamide $^1$H NMR (200 MHz CDCl$_3$), δ: 1.21-1.29 (m, 9H), 3.30-3.37 (m, 1H), 3.41-3.51 (m, 2H), 3.82 (s, 3H), 4.91 (s, 2H), 5.04 (s, 2H), 6.55 (s, 1H), 6.78 (d, J=8.8 Hz, 2H), 6.94-7.0 (m, 1H), 7.16-7.19 (m, 2H), 7.25-7.30 (m, 3H), 7.34-7.40 (m, 5H), 7.49 (d, J=8.8 Hz, 2H), 7.58 (s, 1H), 9.19 (s, 1H).
$^{13}$C NMR (50 MHz CDCl$_3$), δ: 14.6, 27.0, 34.4, 55.5, 70.1, 71.0, 97.5, 110.9, 113.7, 114.2, 115.7, 126.5, 127.3, 128.0, 128.6, 128.7, 129.3, 129.9, 136.5, 136.8, 151.0, 155.3, 158.7, 159.8, 160.5, 162.4, 164.1.
[M+H]$^+$ 620.9.

Step ix: 5-(2,4-dihydroxy-5-isopropyl-phenyl)-4-(4-methoxy-benzoylamino)-isoxazole-3-carboxylic acid ethylamide $^1$H NMR (400 MHz DMSO), δ: 1.04-1.28 (m, 9H), 3.03-3.08 (m, 1H), 3.19-3.23 (m, 2H), 3.82 (s, 3H), 6.47 (s, 1H), 7.02 (d, J=8.8 Hz, 2H), 7.23 (s, 1H), 7.87 (d, J=8.8 Hz, 2H), 8.61 (t, J=5.6 Hz, 1H), 9.56 (br, 1H), 9.82 (s, 1H), 10.08 (br, 1H).
$^{13}$C NMR (100 MHz DMSO), δ: 14.5, 22.6, 25.6, 33.6, 55.4, 102.7, 104.5, 112.6, 113.6, 125.8, 126.1, 126.5, 129.4, 155.9, 157.7, 158.7, 162.0, 163.5, 165.2.
[M+H]$^+$ 440.4.

Examples 12-21 were synthesized according to the procedure described for example 11 (step viii to step ix), starting from the common intermediate 4-amino-5-(2,4-bis-benzyloxy-5-isopropyl-phenyl)-isoxazole-3-carboxylic acid ethylamide and using the adequate acid chloride in step viii.

Example 12

4-acetylamino-5-(2,4-dihydroxy-5-isopropyl-phenyl)-isoxazole-3-carboxylic acid ethylamide SST0113AA1

Step viii: 4-acetylamino-5-(2,4-bis-benzyloxy-5-isopropyl-phenyl)-isoxazole-3-carboxylic acid ethylamide $^1$H NMR (200 MHz CDCl$_3$), δ: 1.22-1.29 (m, 9H), 1.77 (s, 3H), 3.28-3.36 (m, 1H), 3.40-3.50 (m, 2H), 5.03 (s, 2H), 5.08 (m, 2H), 6.58 (s, 1H), 6.83 (br, 1H), 7.31-7.42 (m, 10H), 7.49 (s, 1H), 8.07 (s, 1H).
[M+H]$^+$ 528.7.

Step ix: 4-acetylamino-5-(2,4-dihydroxy-5-isopropyl-phenyl)-isoxazole-3-carboxylic acid ethylamide $^1$H NMR (400 MHz DMSO), δ: 1.07-1.12 (m, 9H), 3.06-3.13 (m, 1H), 3.21-3.26 (m, 2H), 6.49 (s, 1H), 7.11 (s, 1H), 8.55 (t, J=6.0 Hz, 1H), 9.15 (br, 1H), 9.81 (s, 1H), 9.90 (br, 1H).

$^{13}$C NMR (100 MHz DMSO), δ: 14.4, 22.4, 22.5, 33.4, 102.6, 104.2, 112.3, 125.9, 126.4, 154.1, 155.8, 157.6, 158.6, 163.3, 169.1.
[M+H]$^+$ 348.5.

Example 13

5-(2,4-dihydroxy-5-isopropyl-phenyl)-4-(2,2-dimethyl-propionylamino)-isoxazole-3-carboxylic acid ethylamide SST0114AA1

Step viii: 5-(2,4-bis-benzyloxy-5-isopropyl-phenyl)-4-(2,2-dimethyl-propionylamino)-isoxazole-3-carboxylic acid ethylamide $^1$H NMR (200 MHz CDCl$_3$), δ: 1.05 (s, 9H), 1.21-1.26 (m, 9H), 3.26-3.35 (m, 1H), 3.44-3.53 (m, 2H), 5.00 (s, 2H), 5.06 (m, 2H), 6.57 (s, 1H), 6.88 (br, 1H), 7.25-7.41 (m, 10H), 7.45 (s, 1H), 8.71 (s, 1H).

Step ix: 5-(2,4-dihydroxy-5-isopropyl-phenyl)-4-(2,2-dimethyl-propionylamino)-isoxazole-3-carboxylic acid ethylamide $^1$H NMR (400 MHz CD$_3$OD), δ: 1.18-1.24 (m, 18H), 3.17-3.24 (m, 1H), 3.48 (q, J=6.8 Hz, 2H), 6.47 (s, 1H), 7.27 (s, 1H).
$^{13}$C NMR (100 MHz CD$_3$OD), δ: 14.8, 23.2, 27.8, 35.6, 40.2, 103.7, 106.2, 111.8, 113.4, 127.7, 129.2, 154.7, 156.7, 159.8, 162.2, 163.6, 179.9.
[M+H]$^+$ 390.5.

Example 14

5-(2,4-dihydroxy-5-isopropyl-phenyl)-4-[(3-methyl-thiophene-2-carbonyl)-amino]-isoxazole-3-carboxylic acid ethylamide SST0115AA1

Step viii: 5-(2,4-bis-benzyloxy-5-isopropyl-phenyl)-4-[(3-methyl-thiophene-2-carbonyl)-amino]-isoxazole-3-carboxylic acid ethylamide $^1$H NMR (200 MHz CDCl$_3$), δ: 1.22-1.28 (m, 9H), 2.33 (s, 3H), 3.23-3.38 (m, 1H), 3.41-3.54 (m, 2H), 4.95 (s, 2H), 5.01 (m, 2H), 6.52 (s, 1H), 6.80 (d, J=5.2 Hz, 1H), 6.89 (br, 1H), 7.09-7.14 (m, 2H), 7.21-7.25 (m, 4H), 7.35-7.39 (m, 5H), 7.55 (s, 1H), 9.0 (s, 1H).

Step ix: 5-(2,4-dihydroxy-5-isopropyl-phenyl)-4-[(3-methyl-thiophene-2-carbonyl)-amino]-isoxazole-3-carboxylic acid ethylamide $^1$H NMR (400 MHz DMSO), δ: 1.07-1.11 (m, 9H), 2.44 (s, 3H), 3.05-3.11 (m, 1H), 3.19-3.25 (m, 2H), 6.52 (s, 1H), 7.01 (d, J=5.2 Hz, 1H), 7.22 (s, 1H), 7.66 (d, J=5.2 Hz, 1H), 8.66 (t, J=5.6 Hz, 1H), 9.12 (s, 1H), 9.89 (s, 1H), 10.22 (br, 1H).
$^{13}$C NMR (100 MHz DMSO), δ: 14.4, 15.2, 22.4, 25.7, 33.3, 33.5, 102.5, 104.4, 112.2, 126.2, 128.2, 130.4, 131.7, 141.1, 153.6, 155.3, 157.6, 157.8, 158.6, 161.1, 162.4.
[M+H]$^+$ 430.6/431.6

Example 15

5-(2,4-dihydroxy-5-isopropyl-phenyl)-4-(3-morpholin-4-yl-propionylamino)-isoxazole-3-carboxylic acid ethylamide SST0116AA1

Step viii: 5-(2,4-bis-benzyloxy-5-isopropyl-phenyl)-4-(3-morpholin-4-yl-propionylamino)-isoxazole-3-carboxylic acid ethylamide $^1$H NMR (200 MHz CDCl$_3$), δ: 1.18-1.25 (m, 9H), 2.22-2.27 (m, 2H), 2.36-2.44 (m, 2H), 2.88-2.86 (m, 4H), 3.20-3.48 (m, 3H), 3.62-3.66 (m, 4H), 4.97 (s, 2H), 5.02 (m, 2H), 6.52 (s, 1H), 6.88 (br, 1H), 7.24-7.37 (m, 10H), 7.42 (s, 1H), 10.66 (s, 1H).

Step ix: 5-(2,4-dihydroxy-5-isopropyl-phenyl)-4-(3-morpholin-4-yl-propionylamino)-isoxazole-3-carboxylic acid ethylamide $^1$H NMR (400 MHz CD$_3$OD), δ: 1.19-1.24 (m, 9H), 2.51-2.54 (m, 6H), 2.71 (t, J=6.8 Hz, 1H), 3.17-3.23 (m, 1H), 3.38 (d, J=7.2 Hz, 2H), 3.61-3.63 (m, 4H), 6.43 (s, 1H), 7.23 (s, 1H).
$^{13}$C NMR (100 MHz CD$_3$OD), δ: 14.9, 23.3, 27.8, 33.5, 35.5, 54.4, 55.2, 67.8, 103.9, 106.8, 113.5, 128.0, 128.9, 155.4, 156.4, 159.8, 161.9, 164.7, 173.8.
[M+H]$^+$ 447.6.

Example 16

4-(3-(4-methylpiperazin-1-yl)propanamido)-N-ethyl-5-(2,4-dihydroxy-5-isopropylphenyl)-isoxazole-3-carboxamide SST0203AA1

Step viii: 5-(2,4-bis(benzyloxy)-5-isopropylphenyl)-4-(3-(4-methylpiperazin-1-yl)-propanamido)-N-ethylisoxazole-3-carboxamide $^1$H NMR (400 MHz CD$_3$Cl), δ: 1.22-1.28 (m, 9H), 2.23 (s, 3H), 2.27 (t, J=6.4 Hz, 2H), 2.30-2.42 (m, 8H), 2.50 (t, J=6.4 Hz, 2H), 3.30-3.34 (m, 1H), 3.44-3.49 (m, 2H), 5.02 (s, 2H), 5.04 (s, 2H), 6.55 (s, 1H), 6.84 (br, 1H), 7.30-7.40 (m, 10H), 7.44 (s, 1H), 9.68 (s, 1H).
$^{13}$C NMR (100 MHz CD$_3$Cl), δ: 14.7, 22.7, 26.6, 32.7, 34.4, 46.1, 52.6, 53.5, 54.8, 70.1, 71.3, 98.3, 110.5, 114.6, 127.0, 127.2, 128.1, 128.7, 130.2, 136.7, 136.8, 152.5, 155.3, 158.6, 159.6, 161.4, 170.3.
[M+H]$^+$ 640.7

Step ix: 4-(3-(4-methylpiperazin-1-yl)propanamido)-N-ethyl-5-(2,4-dihydroxy-5-isopropylphenyl)-isoxazole-3-carboxamide $^1$H NMR (400 MHz CD$_3$OD), δ: 1.19-1.24 (m, 9H), 2.40 (s, 3H), 2.52 (t, J=6.4 Hz, 2H), 2.55-2.71 (m, 8H), 2.75 (t, J=6.4 Hz, 2H), 3.14-3.25 (m, 1H), 3.34-3.39 (m, 2H), 6.44 (s, 1H), 7.23 (s, 1H).
$^{13}$C NMR (100 MHz CD$_3$OD), δ: 14.7, 23.1, 27.6, 27.6, 33.6, 35.3, 45.2, 52.4, 54.4, 55.3, 103.8, 106.7, 113.3, 127.8, 128.7, 155.3, 156.2, 159.6, 161.7, 164.4, 173.5.
[M+H]$^+$ 460.4.

Example 17

1H-indole-6-carboxylic acid [5-(2,4-dihydroxy-5-isopropyl-phenyl)-3-ethyl carbamoyl-isoxazole-4-yl]-amide SST0220AA1

Step ix: 1H-indole-6-carboxylic acid [5-(2,4-dihydroxy-5-isopropyl-phenyl)-3-ethyl carbamoyl-isoxazol-4-yl]-amide $^1$H NMR (300 MHz CD$_3$OD), δ: 1.16-1.28 (m, 9H), 3.18 (m, 1H), 3.40 (q, 2H), 6.44 (s, 1H), 6.53 (d, 1H), 7.35 (s, 1H), 7.42 (d, 1H), 7.53 (d, 1H), 7.63 (d, 1H), 8.01 (s, 1H).
[M+H]$^+$ 449.09.

Example 18

5-(2,4-dihydroxy-5-isopropyl-phenyl)-4-(4-morpholin-4-yl-methyl-benzoyl amino)-isoxazole-3-carboxylic acid ethylamide hydrochloride SST0201CL1

Step ix: 5-(2,4-dihydroxy-5-isopropyl-phenyl)-4-(4-morpholin-4-yl-methyl-benzoyl amino)-isoxazole-3-carboxylic acid ethylamide hydrochloride $^1$H NMR (300 MHz, DMSO), δ: 1.03-1.09 (m, 9H), 3-3.27 (m, 7H), 3.72 (m, 2H), 3.93 (m, 2H), 4.41 (s, 2H), 6.50 (s, 1H), 7.22 (s, 1H), 7.69 (d, 2H), 7.97 (d, 2H), 8.67 (t, 1H), 9.78 (s, 1H), 9.86 (s, 1H), 10.1 (s, 1H), 10.80 (s, 1H).
[M+H]$^+$ 509.

Example 19

4-(cyclohexanecarbonyl-amino)-5-(2,4-dihydroxy-5-isopropyl-phenyl)-isoxazole-3-carboxylic acid ethylamide SST0221AA1

Step ix: 4-(cyclohexanecarbonyl-amino)-5-(2,4-dihydroxy-5-isopropyl-phenyl)-isoxazole-3-carboxylic acid ethylamide $^1$H NMR (300 MHz CD$_3$OD), δ: 1.18-1.41 (m, 13H), 1.7 (m, 2H), 1.78 (m, 2H), 1.9 (m, 2H), 2.3 (m, 1H), 3.18 (m, 1H), 3.34 (q, 2H), 6.44 (s, 1H), 7.24 (s, 1H).
[M+H]$^+$ 416.3.

Example 20

5-(2,4-dihydroxy-5-isopropyl-phenyl)-4-[(trans-4-pentyl-cyclohexanecarbonyl)-amino]-isoxazole-3-carboxylic acid ethylamide SST0222AA1

Step ix: 5-(2,4-dihydroxy-5-isopropyl-phenyl)-4-[(trans-4-pentyl-cyclohexanecarbonyl)-amino]-isoxazole-3-carboxylic acid ethylamide $^1$H NMR (300 MHz CD$_3$OD), δ: 0.87-1.02 (m, 5H), 1.18-1.51 (m, 20H), 1.84 (m, 2H), 1.95 (m, 2H), 2.25 (m, 1H), 3.19 (m, 1H), 3.37 (q, 2H), 6.44 (s, 1H), 7.24 (s, 1H).
[M+H]$^+$ 486.3.

Example 21

5-(2,4-dihydroxy-5-isopropyl-phenyl)-4-[(4-trifluoromethyl-cyclohexane carbonyl)-amino]-isoxazole-3-carboxylic acid ethylamide SST0223AA1

Step ix: 5-(2,4-dihydroxy-5-isopropyl-phenyl)-4-[(4-trifluoromethyl-cyclohexane carbonyl)-amino]-isoxazole-3-carboxylic acid ethylamide $^1$H NMR (300 MHz CD$_3$OD), δ: 1.18-1.20 (m, 9H), 1.65-1.75 (m, 6H), 2.06-2.20 (m, 3H), 2.64 (m, 1H), 3.19 (m, 1H), 3.37 (q, 2H), 6.44 (s, 1H), 7.24 (s, 1H).
[M+H]$^+$ 484.2.

Example 22 was synthesized according to the procedure described in examples 11-21 (step viii to step ix), including a further step corresponding to step v of scheme 1 between step viii and step ix.

Example 22

N$^5$-(3-(ethylcarbamoyl)-5-(2,4-dihydroxy-5-isopropylphenyl)-isoxazol-4-yl)-N$^3$-ethylisoxazole-3,5-dicarboxamide SST0211AA1

Step viii: methyl 5-(3-(ethylcarbamoyl)-5-(2,4-bis(benzyloxy)-5-isopropylphenyl)-isoxazol-4-ylcarbamoyl)-isoxazole-3-carboxylate $^1$H NMR (200 MHz CDCl$_3$), δ: 1.22-1.32 (m, 9H), 3.28-3.42 (m, 1H), 3.44-3.56 (m, 2H), 4.01 (s, 3H), 4.97, (s, 2H), 5.08 (s, 2H), 6.59 (s, 1H), 6.84 (br, 1H), 7.06 (s, 1H), 7.14-7.19 (m, 2H), 7.26-7.29 (m, 2H), 7.38-7.42 (m, 6H), 7.56 (s, 1H), 9.43 (s, 1H).
[M+H]$^+$ 639.7.

Step v: N$^5$-(3-(ethylcarbamoyl)-5-(2,4-bis(benzyloxy)-5-isopropylphenyl)-isoxazol-4-yl)-N$^3$-ethylisoxazole-3,5-dicarboxamide $^1$H NMR (400 MHz CDCl$_3$), δ: 1.24-1.30 (m, 12H), 3.30-3.38 (m, 1H), 3.47-3.54 (m, 4H), 4.94 (s, 2H), 5.10, (s, 2H), 6.57 (s, 1H), 6.78 (br, 1H), 6.89 (br, 1H), 7.10 (s, 1H), 7.13-7.15 (m, 2H), 7.24-7.27 (m, 2H), 7.40-7.41 (m, 6H), 7.56 (s, 1H), 9.50 (s, 1H).
[M+H]$^+$ 652.6.

Step ix: N$^5$-(3-(ethylcarbamoyl)-5-(2,4-dihydroxy-5-isopropylphenyl)-isoxazol-4-yl)-N$^3$-ethylisoxazole-3,5-dicarboxamide $^1$H NMR (400 MHz DMSO), δ: 1.05-1.12 (m, 12H), 3.04-3.08 (m, 1H), 3.19-3.28 (m, 4H), 3.31 (s, 1H), 6.47 (s, 1H), 7.18 (s, 1H), 7.44 (s, 1H), 8.71 (t, J=5.6 Hz, 1H), 8.95 (t, J=5.6 Hz, 1H), 9.88 (s, 1H), 10.08 (s, 1H).
$^{13}$C NMR (100 MHz DMSO), δ: 14.3, 14.4, 22.4, 25.6, 33.5, 33.8, 102.6, 104.0, 106.0, 126.2, 126.5, 154.1, 154.2, 155.2, 157.2, 158.0, 158.3, 159.4, 163.6, 163.7.
[M+H]$^+$ 472.3.

Examples 23-26 were synthesized according to the procedure described in example 12 (step viii to step ix) using the adequate acid chloride in step viii.

Example 23

5-(2,4-dihydroxy-5-isopropyl-phenyl)-4-[(4-methoxy-cyclohexanecarbonyl)-amino]-isoxazole-3-carboxylic acid ethylamide SST0226AA1

$^1$H NMR (300 MHz, DMSO), δ: 1.04-1.10 (m, 9H), 1.33-1.82 (m, 8H), 2.26 (m, 1H), 3.06 (m, 1H), 3.16 (s, 3H), 3.21 (q, 2H), 3.35 (m, 1H), 6.47 (s, 1H), 7.09 (s, 1H), 8.47 (t, 1H), 9.76 (s, 1H).
[M+H]$^+$ 446.4.

Example 24

4-[(4-tert-butyl-cyclohexanecarbonyl)-amino]-5-(2,4-dihydroxy-5-isopropyl-phenyl)-isoxazole-3-carboxylic acid ethylamide SST0227AA1

$^1$H NMR (300 MHz, DMSO), δ: 0.73 (s, 6H), 0.8 (s, 3H), 0.93 (m, 2H), 1.04-1.1 (m, 9H), 1.18-2.07 (m, 8H), 3.06 (m, 1H), 3.19 (q, 2H), 6.46 (s, 1H), 7.10 (s, 1H), 8.48 (t, 1H), 9.76 (s, 1H).
[M+H]$^+$ 472.2.

Example 25

4-[(trans-4-amino-cyclohexanecarbonyl)-amino]-5-(2,4-dihydroxy-5-isopropyl-phenyl)-isoxazole-3-carboxylic acid ethylamide hydrochloride SST0228CL1

$^1$H NMR (300 MHz, CD$_3$OD), δ: 1.18-1.24 (m, 9H), 1.43-2.12 (m, 7H), 3.14 (m, 2H), 3.19 (m, 1H), 3.40 (q, 2H), 4.4 (s, 1H), 6.44 (s, 1H), 7.23 (s, 1H).
[M+H]$^+$ 431.2.

Example 26

4-[(trans-4-aminomethyl-cyclohexanecarbonyl)-amino]-5-(2,4-dihydroxy-5-isopropyl-phenyl)-isoxazole-3-carboxylic acid ethylamide hydrochloride SST0229CL1

$^1$H NMR (300 MHz, CD$_3$OD) δ: 1.17-1.24 (m, 9H), 1.4-2.05 (m, 9H), 2.33 (m, 1H), 2.79 (d, 2H), 3.20 (m, 1H), 3.37 (q, 2H), 6.43 (s, 1H), 7.23 (s, 1H).
[M+H]$^+$ 445.2.

Example 27 was synthesized following the procedure as described in scheme 2, the first step corresponding to the reaction conditions described for step ix of scheme 1.

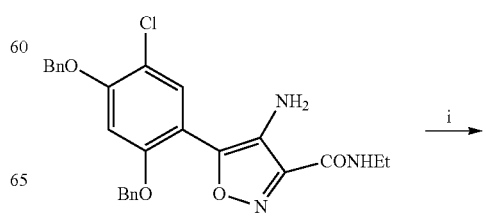

Scheme 2

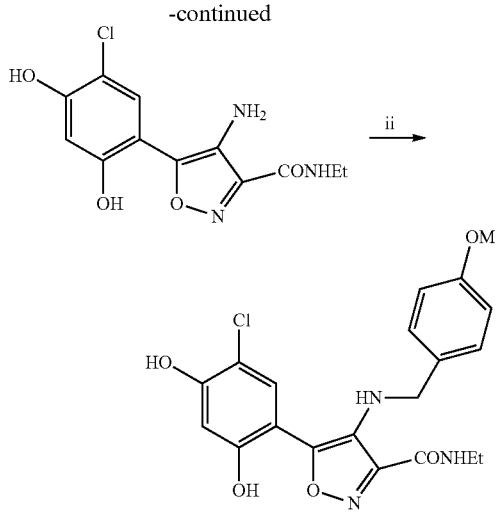

i: BCl₃, DCM; ii: p-methoxybenzaldehyde, NaCNBH₄, 1% AcOH, MeOH

Example 27

4-(4-methoxybenzylamino)-5-(5-chloro-2,4-dihydroxyphenyl)-N-ethylisoxazole-3-carboxamide SST0207AA1

Step i: 4-amino-5-(5-chloro-2,4-dihydroxyphenyl)-N-ethylisoxazole-3-carboxamide $^1$H NMR (400 MHz DMSO), δ: 1.11 (t, J=7.2 Hz, 3H), 3.23-3.30 (m, 2H), 4.70 (br, 2H), 6.67 (s, 1H), 7.35 (s, 1H), 8.73 (t, J=6.0 Hz, 1H), 10.54 (br, 2H).
$^{13}$C NMR (100 MHz DMSO), δ: 14.5, 33.3, 104.0, 107.8, 110.9, 124.4, 128.0, 148.9, 150.7, 153.4, 154.6, 160.0.
[M+H]$^+$ 298.1/300.1.

Step ii: 4-(4-methoxybenzylamino)-5-(5-chloro-2,4-dihydroxyphenyl)-N-ethylisoxazole-3-carboxamide A solution of 4-amino-5-(5-chloro-2,4-dihydroxyphenyl)-N-ethylisoxazole-3-carboxamide (298 mg, 1 mmol) and p-methoxy benzaldehyde (2 mmol) in a mixture di MeOH/AcOH (1%) (15 ml) was refluxed over night. Sodium cyanoborohydride (125 mg, 2 mmol) was added to the cooled suspension and the mixture was stirred for 3 hours. The residue was treated with aqueous 5% NaHCO₃ (10 ml) and extracted with AcOEt. The combined organic extracts were washed with brine, dried, and evaporated under reduced pressure. The crude reaction material was purified by chromatography (AcOEt/light petroleum).

$^1$H NMR (400 MHz CDCl₃), δ: 1.25 (t, J=7.6 Hz, 3H), 3.44-3.48 (m, 2H), 3.76 (s, 3H), 3.83-3.85 (m, 2H), 4.84 (br, 1H), 5.76 (s, 1H), 6.67 (s, 1H), 6.71 (br, 1H), 6.78 (d, J=8.2 Hz, 2H), 7.14 (d, J=8.2 Hz, 2H), 7.62 (s, 1H), 12.02 (br, 1H).
$^{13}$C NMR (100 MHz CDCl₃), δ: 14.6, 34.3, 54.9, 55.3, 106.1, 108.1, 111.7, 114.0, 120.2, 127.0, 127.9, 130.8, 152.3, 154.5, 157.2, 159.4, 159.5, 163.0.
[M+H]$^+$ 418.3/420.2.

Examples 28-32 were synthesized from the common intermediate 4-amino-5-(5-chloro-2,4-dihydroxyphenyl)-N-ethylisoxazole-3-carboxamide following the procedure described in scheme 2-step ii using the adequate aldehyde or ketone derivative instead.

Example 28

4-((3-methylthiophen-2-yl)methylamino)-5-(5-chloro-2,4-dihydroxyphenyl)-N-ethylisoxazole-3-carboxamide SST0206AA1

$^1$H NMR (400 MHz CDCl₃), δ: 1.24 (t, J=7.2 Hz, 3H), 2.10 (s, 3H), 3.42-3.46 (m, 2H), 4.02 (s, 2H), 4.89 (br, 1H), 5.75 (s, 1H), 6.67-6.71 (m, 3H), 7.08-7.09 (m, 1H), 7.64 (s, 1H), 11.68 (br, 1H).
$^{13}$C NMR (100 MHz CDCl₃), δ: 13.3, 14.6, 34.2, 46.7, 106.4, 107.9, 111.8, 119.7, 124.5, 127.0, 130.0, 130.8, 136.8, 152.5, 154.6, 156.9, 159.3, 163.0.
[M+H]$^+$ 408.2/410.2.

Example 29

5-(5-chloro-2,4-dihydroxyphenyl)-4-(cyclohexylamino)-N-ethylisoxazole-3-carboxamide SST0208AA1

$^1$H NMR (400 MHz CDCl₃), δ: 1.10-1.29 (m, 7H), 1.57-1.82 (m, 6H), 2.61 (br, 1H), 3.45-3.53 (m, 2H), 4.48 (br, 1H), 5.80 (br, 1H), 6.65 (s, 1H), 6.85 (br, 1H), 7.69 (s, 1H), 12.18 (br, 1H).
$^{13}$C NMR (100 MHz CDCl₃), δ: 14.6, 24.8, 25.4, 32.0, 34.3, 59.8, 106.2, 108.2, 111.6, 119.2, 127.0, 152.6, 154.5, 157.2, 159.6, 163.3.
[M+H]$^+$ 380.4/382.3.

Example 30

4-(1-methylpiperidin-4-ylamino)-5-(5-chloro-2,4-dihydroxyphenyl)-N-ethylisoxazole-3-carboxamide SST0209AA1

$^1$H NMR (400 MHz CD₃OD), δ: 1.22 (t, J=7.6 Hz, 3H), 1.62-1.70 (m, 2H), 2.05-2.09 (m, 2H), 2.78 (s, 3H), 2.87-2.96 (m, 2H), 3.11-3.17 (m, 1H), 3.38-3.48 (m, 4H), 6.49 (s, 1H), 7.59 (s, 1H).
$^{13}$C NMR (100 MHz CD₃OD), δ: 14.8, 30.3, 35.1, 43.5, 54.4, 54.6, 106.6, 108.0, 113.9, 119.8, 129.5, 157.3, 158.0, 161.3, 163.9.
[M+H]$^+$ 395.4/397.3.

Example 31

Methyl 5-((3-(ethylcarbamoyl)-5-(5-chloro-2,4-dihydroxyphenyl)isoxazol-4-ylamino)methyl)isoxazole-3-carboxylate SST0210AA1

$^1$H NMR (400 MHz CD₃OD), δ: 1.22 (t, J=7.6 Hz, 3H), 3.38 (q, J=7.6 Hz, 2H), 3.90 (s, 3H), 4.26 (s, 2H), 6.45 (s, 1H), 6.49 (s, 1H), 7.32 (s, 1H).
$^{13}$C NMR (100 MHz CD₃OD), δ: 14.7, 35.1, 44.1, 53.2, 104.6, 105.7, 108.2, 113.5, 123.1, 130.3, 153.6, 156.7, 157.1, 157.6, 160.2, 161.3, 161.6, 173.2.
[M+H]$^+$ 437.2/438.4/439.2.

Example 32

4-((3-(hydroxymethyl)isoxazol-5-yl)methylamino)-5-(5-chloro-2,4-dihydroxyphenyl)-N-ethylisoxazole-3-carboxamide SST0212AA1

Sodium borohydride (2 eq) was added portionwise at 0° C. to a solution of methyl 5-((3-(ethylcarbamoyl)-5-(5-chloro- 2,4-dihydroxyphenyl) isoxazol-4-ylamino)methyl)isoxazole-3-carboxylate (0.34 mmol, 150 mg) in EtOH 95% (5 ml). After 30 min, few drops of a 5% HCl solution were added to the mixture and the solvent was evaporated under vacuo. The crude reaction mixture was diluted with $H_2O$ (10 ml) and extracted with AcOEt (2×10 ml). The combined organic phases were washed with brine, dried and filtered. Solvent was removed under vacuo and the crude product was purified by flash chromatography on silica gel (AcOEt/light petroleum).

$^1$H NMR (400 MHz $CD_3OD$), δ: 1.22 (t, J=7.6 Hz, 3H), 3.39 (q, J=7.6 Hz, 2H), 4.18 (s, 2H), 4.50 (s, 2H), 6.15 (s, 1H), 6.51 (s, 1H), 7.39 (s, 1H).

$^{13}$C NMR (100 MHz $CD_3OD$), δ: 14.8, 35.1, 44.3, 56.6, 103.0, 105.8, 108.3, 113.5, 123.2, 130.3, 153.6, 156.9, 157.6, 160.1, 161.7, 165.4, 171.0.

[M+H]$^+$ 409.1/411.1.

Example 33 was synthesized following the procedure as described in scheme 3.

Scheme 3

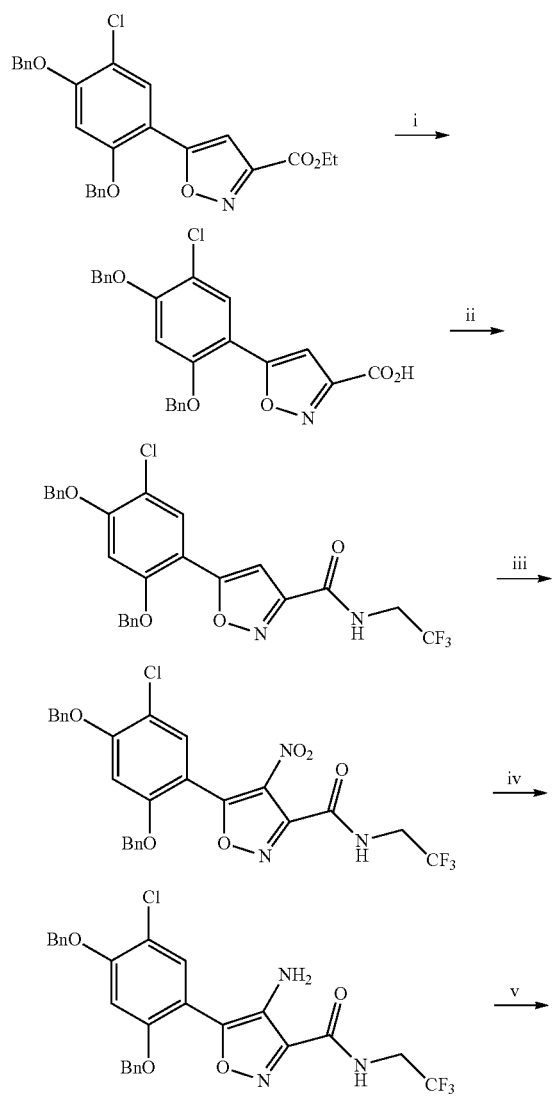

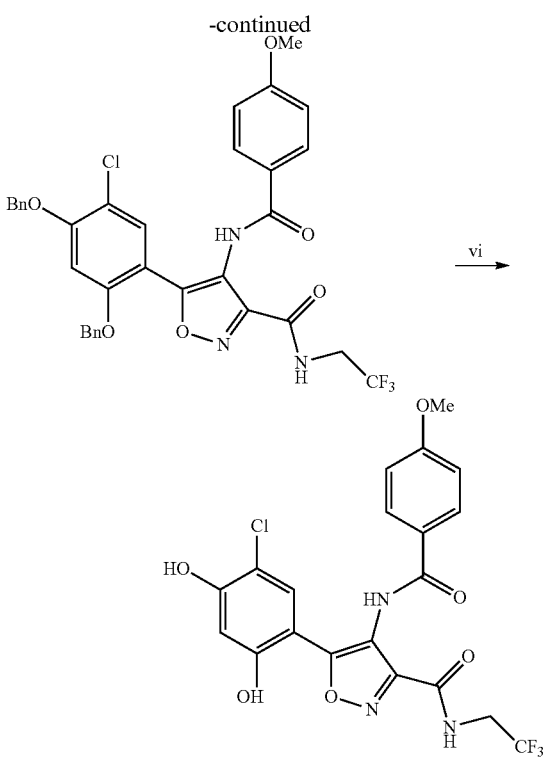

i: NaOH 6N, MeOH; ii: a) $SOCl_2$, toluene; b) TEA, DCM, 2,2,2-trifluoroethylamine.HCl; iii: $HNO_3$, $Ac_2O$; iv: $H_2O$, THF, $NH_4Cl$, Zn; v: p-metoxybenzoylchloride, TEA, DCM; vi: $BCl_3$, DCM Example 33

4-(4-methoxybenzamido)-5-(5-chloro-2,4-dihydroxyphenyl)-N-(2,2,2-trifluoroethyl)-isoxazole-3-carboxamide SST0204AA1

Step i: 5-[2,4-bis(benzyloxy)-5-chlorophenyl]-isoxazole-3-carboxylic acid

A mixture of ethyl 5-(2,4-bis(benzyloxy)-5-chlorophenyl) isoxazole-3-carboxylate (200 mg, 0.43 mmol), methanol (10 ml), water (6-7 ml), and LiOH (16 mg, 0.65 mmol) was allowed to stand at 50-60° C. for 24 h. The solution was concentrated under vacuo to remove methanol, and the remaining aqueous solution was extracted with $Et_2O$ to remove traces of unreacted starting material. The aqueous solution was acidified with 1 M HCl and extracted with three portions of AcOEt. The combined organic extracts were washed with saturated aqueous sodium chloride and dried over sodium sulfate. Removal of the solvent under reduced pressure afforded a residue, which was chromatographed on silica gel (DCM/methanol: 9/1).

$^1$H NMR (200 MHz DMSO), δ: 5.34 (s, 2H), 5.38 (s, 2H), 6.91, (s, 1H), 7.36-7.51 (m, 11H), 7.90 (s, 1H), 13.95, (br, 1H).

[M+H]$^+$ 436.2/438.4.

Step ii: 5-[2,4-bis(benzyloxy)-5-chlorophenyl]-N-(2,2,2-trifluoroethyl)isoxazole-3-carboxamide Thionyl chloride (0.26 ml, 3.55 mmol) was added to a suspension of 3-(2,4-bis(benzyloxy)-5-chlorophenyl)isoxazole-5-carboxylic acid (310 mg, 0.7 mmol) in toluene (5 ml).

The resulting mixture was heated to 110° C. for 5 hours and then allowed to return to RT. After concentration under vacuo, DCM (15 ml) was added to the solution, followed by addition of 2,2,2-trifluoroethylamine hydrochloride (114 mg, 0.84 mmol), TEA (0.22 ml, 1.6 mmol). The mixture was stirred at RT overnight. The solution was diluted with DCM (15 ml) washed with HCl 1N (15 ml), water (15 ml) and brine (15 ml), dried over sodium sulphate and evaporated in vacuo. The residue was chromatographed on silica gel (eluent, $Et_2O$/light petroleum).

$^1$H NMR (400 MHz $CDCl_3$), δ: 4.08-4.12 (m, 2H), 5.12 (s, 2H), 5.16 (s, 2H), 6.61, (s, 1H), 7.10-7.12 (m, 2H), 7.33-7.40 (m, 10H), 7.98 (s, 1H).

$[M+H]^+$ 517.5/518.5/519.3.

Step iii: 5-[2,4-bis(benzyloxy)-5-chlorophenyl]-N-(2,2,2-trifluoroethyl)-4-nitroisoxazole-3-carboxamide This step was executed following the procedure as described in step vi of scheme 1.

$^1$H NMR (400 MHz $CDCl_3$), δ: 4.07-4.15 (m, 2H), 5.01 (s, 2H), 5.10 (s, 2H), 6.59, (s, 1H), 6.93, (br, 1H), 7.22-7.27 (m, 2H), 7.32-7.40 (m, 8H), 7.68 (s, 1H).

$[M+H]^+$ 562.5/563.3/564.4.

Step iv: 5-(2,4-bis-(benzyloxy)-5-chlorophenyl)-4-amino-N-(2,2,2-trifluoroethyl)isoxazole-3-carboxamide This step was executed following the procedure as described in step vii of scheme 1.

$^1$H NMR (200 MHz $CDCl_3$), δ: 3.97-4.14 (m, 2H), 4.35 (br, 2H), 5.04 (s, 2H), 5.16 (s, 2H), 6.65, (s, 1H), 7.08, (br, 1H), 7.31-7.44 (m, 10H), 7.65 (s, 1H).

$[M+H]^+$ 532.3/533.6/534.3.

Step v: 5-[2,4-bis(benzyloxy)-5-chlorophenyl]-4-(4-methoxybenzamido)-N-(2,2,2-trifluoroethyl)-isoxazole-3-carboxamide This step was executed following the procedure as described in step viii of scheme 1.

$^1$H NMR (400 MHz $CDCl_3$), δ: 3.85 (s, 3H), 4.04-4.12 (m, 2H), 4.86 (br, 2H), 5.11 (s, 2H), 5.16 (s, 2H), 6.58 (s, 1H), 6.82 (d, J=8.8 Hz, 2H), 7.12-7.12 (m, 2H), 7.24-7.27 (m, 4H), 7.35-7.43 (m, 6H), 7.51 (d, J=8.8 Hz, 2H), 7.45 (s, 1H), 9.04 (s, 1H).

$[M+H]^+$ 532.3/533.6/534.3.

Step vi: 4-(4-methoxybenzamido)-5-(5-chloro-2,4-dihydroxyphenyl)-N-(2,2,2-trifluoroethyl)-isoxazole-3-carboxamide This step was executed following the procedure as described in step ix of scheme 1.

$^1$H NMR (400 MHz DMSO), δ: 3.82 (s, 3H), 3.99-4.04 (m, 2H), 6.62 (s, 1H), 7.02 (d, J=8.8 Hz, 2H), 7.43 (s, 1H), 7.86 (d, J=8.8 Hz, 2H), 9.36-9.39 (m, 1H), 9.80 (br, 1H), 10.66 (br, 2H).

$^{13}$C NMR (100 MHz DMSO), δ: 55.3, 59.7 (q, J=30 Hz), 104.0, 106.0, 113.5, 122.9, 126.1, 124.3 (q, J=255 Hz), 139.4, 154.8, 155.9, 159.6, 161.7, 161.9, 164.8.

$[M+H]^+$ 486.3/487.5/488.1.

Example 34 was synthesized following the procedure as described in example starting from the common intermediate 5-[2,4-bis(benzyloxy)-5-chlorophenyl]-isoxazole-3-carboxylic acid and using 3,3-difluoro-azetidine instead of 2,2,2-trifluoroethyl in step ii.

Example 34

4-(4-methoxybenzamido)-5-(5-chloro-2,4-dihydroxyphenyl)-isoxazol-3-yl-(3,3-difluoroazetidin-1yl)-methanone SST0205AA1

Step ii: 5-(2,4-bis-(benzyloxy)-5-chlorophenyl)isoxazol-3-yl)(3,3-difluoroazetidin-1-yl)-methanone $^1$H NMR (200 MHz $CDCl_3$), δ: 4.46-4.59 (m, 2H), 4.84-4.97 (m, 2H), 5.11 (s, 2H), 5.15 (s, 2H), 6.60, (s, 1H), 7.09 (s, 2H), 7.35-7.41 (m, 10H), 7.97 (s, 1H).

$[M+H]^+$ 511.4/512.5/513.5.

Step iii: (5-(2,4-bis-(benzyloxy)-5-chlorophenyl)-4-nitroisoxazol-3-yl)(3,3-difluoroazetidin-1-yl)-methanone $^1$H NMR (400 MHz $CDCl_3$), δ: 4.52-4.58 (m, 4H), 4.99 (s, 2H), 5.14 (s, 2H), 6.62, (s, 1H), 7.25-7.27, (m, 2H), 7.35-7.41 (m, 8H), 7.66 (s, 1H).

$[M+H]^+$ 556.5/557.5/558.4.

Step iv: (5-(2,4-bis-(benzyloxy)-5-chlorophenyl)-4-aminoisoxazol-3-yl)(3,3-difluoroazetidin-1-yl)-methanone $^1$H NMR (200 MHz $CDCl_3$), δ: 4.43-4.55 (m, 4H), 4.83-4.95 (m, 2H), 5.03 (s, 2H), 5.15 (s, 2H), 6.64, (s, 1H), 7.29-7.43 (m, 10H), 7.64 (s, 1H).

$[M+H]^+$ 526.4/527.5/528.5.

Step v: 5-[2,4-bis(benzyloxy)-5-chlorophenyl]-4-(4-methoxybenzamido)-isoxazol-3-yl-(3,3-difluoroazetidin-1-yl)-methanone $^1$H NMR (200 MHz $CDCl_3$), δ: 3.83 (s, 3H), 4.46-4.60 (m, 2H), 4.88-5.0 (m, 4H), 5.11 (s, 2H), 6.59 (s, 1H), 6.80 (d, J=9.2 Hz, 2H), 7.10-7.14 (m, 2H), 7.27-7.29 (m, 2H), 7.34-7.49 (m, 8H), 7.75 (s, 1H), 9.18 (s, 1H).

$[M+H]^+$ 660.7/661.6/662.5.

Step vi: 4-(4-methoxybenzamido)-5-(5-chloro-2,4-dihydroxyphenyl)-isoxazol-3-yl-(3,3-difluoroazetidin-1yl)-methanone $^1$H NMR (400 MHz DMSO), δ: 3.82 (s, 3H), 4.46-4.52 (m, 2H), 4.74-4.80 (m, 2H), 6.66 (s, 1H), 7.02 (d, J=8.8 Hz, 2H), 7.47 (s, 1H), 7.86 (d, J=8.8 Hz, 2H), 9.88 (br, 1H), 10.72 (br, 1H), 10.66 (br, 2H).

$^{13}$C NMR (100 MHz DMSO), δ: 55.4, 59.9 (t, J=28 Hz), 63.2 (t, J=28 Hz), 104.0, 105.9, 110.3, 113.5, 113.6, 116.2 (t, J=270 Hz), 125.4, 126.2, 129.4, 150.2, 153.5, 155.9, 160.2, 161.4, 162.1, 164.7.

$[M+H]^+$ 480.1/481.5/482.2.

Example 35 was synthesized according to the procedure described in example 1 (steps v-ix), using N-methyl piperazine instead of ethylamine in step v.

Example 35

5-(5-chloro-2,4-dihydroxy-phenyl)-4-(4-methoxy-benzoylamino)-isoxazol-3-yl-(4-methylpiperazin-1-O-methanone SST0123AA1

Step v: [5-(2,4-bis-benzyloxy-5-chloro-phenyl)-isoxazol-3-yl]-(4-methyl-piperazin-1-yl)-methanone N-methylpiperazine (25.4 mmol) was added to a suspension of ethyl 5-(2,4-bis(benzyloxy)-5-chlorophenyl)isoxazole-3-carboxylate (2.1 mmol) in EtOH (5 ml) and the reaction mixture was heated to 90° C. under stirring for 18 h. The reaction mixture was poured into a mixture of water (15 ml) and AcOEt (30 ml). After standard extraction, the organic layer was washed with water and brine, dried over $Na_2SO_4$, and evaporated. The resulting solid was purified by silica gel column chromatography ($CHCl_3$/MeOH: 95/0.5) to give the desired compound (620 mg, 57%).

$^1$H NMR (200 MHz $CDCl_3$), δ: 2.32 (s, 3H), 2.45-2.50 (m, 4H), 3.77-3.84 (m, 4H), 5.11 (s, 2H), 5.13 (s, 2H), 6.60 (s, 1H), 6.89 (s, 1H), 7.36-7.41 (m, 10H), 7.97 (s, 1H).
[M+H]$^+$ 518.8/519.9

Step vi: [5-(2,4-bis-benzyloxy-5-chloro-phenyl)-4-nitro-isoxazol-3-yl]-(4-methyl-piperazin-1-yl)-methanone $^1$H NMR (200 MHz $CDCl_3$), δ: 2.23 (s, 3H), 2.46-2.64 (m, 4H), 3.24-3.42 (m, 4H), 4.94 (s, 2H), 5.11 (s, 2H), 6.94 (s, 1H), 7.05-7.16 (m, 10H), 7.70 (s, 1H).

Step vii: [4-amino-5-(2,4-bis-benzyloxy-5-chloro-phenyl)-isoxazol-3-yl]-(4-methyl-piperazin-1-yl)-methanone $^1$H NMR (200 MHz $CD_3OD$), δ: 2.23 (s, 3H), 2.40-2.63 (m, 4H), 3.27-3.48 (m, 4H), 4.94 (s, 2H), 5.11 (s, 2H), 6.76 (s, 1H), 7.05-7.16 (m, 10H), 7.60 (s, 1H).

Step viii: N-[5-(2,4-bis-benzyloxy-5-chloro-phenyl)-3-(4-methyl-piperazine-1-carbonyl)-isoxazol-4-yl]-4-methoxy-benzamide $^1$H NMR (200 MHz $CD_3OD$), δ: 2.25 (s, 3H), 2.30-2.42 (m, 4H), 3.11-3.35 (m, 4H), 3.82 (s, 3H), 5.01 (s, 2H), 5.25 (s, 2H), 6.60 (s, 1H), 7.20-7.38 (m, 12H), 7.66 (d, J=8.0 Hz, 2H), 7.72 (s, 1H).

Step ix: N-[5-(5-chloro-2,4-dihydroxy-phenyl)-3-(4-methyl-piperazine-1-carbonyl)-isoxazol-4-yl]-4-methoxy-benzamide $^1$H NMR (200 MHz $CD_3OD$), δ: 2.28 (s, 3H), 2.50-2.67 (m, 4H), 3.24-3.43 (m, 4H), 3.80 (s, 3H), 6.47 (s, 1H), 7.59 (s, 1H), 7.65 (d, J=8.2 Hz, 2H), 7.85 (d, J=8.2 Hz, 2H).
[M+H]$^+$ 487.9/488.9

Preparation 1 was synthesized according to the procedure described in example 1 (step ix), starting from 5-(2,4-bis-benzyloxy-5-chloro-phenyl)-4-nitro-isoxazole-3-carboxylic acid ethylamide.

Preparation 1

4-nitro-5-(5-chloro-2,4-dihydroxy-phenyl)-isoxazole-3-carboxylic acid ethylamide SST0068AA1

This compound was obtained following the procedure of step ix as described in example 1 starting from 5-(2,4-bis-benzyloxy-5-chloro-phenyl)-4-nitro-isoxazole-3-carboxylic acid ethylamide.

$^1$H NMR (200 MHz $CD_3OD$), δ: 1.25 (t, J=7.2 Hz, 3H), 3.41-3.45 (q, J=7.2 Hz, 2H), 6.57 (s, 1H), 7.53 (s, 1H).
$^{13}$C NMR (400 MHz, $CDCl_3$), δ: 14.77, 33.06, 112.99, 117.25, 117.87, 122.56, 133.53, 145.18, 150.23, 152.31, 154.05, 162.69.

Preparation 2

4-amino-5-(5-chloro-2,4-dihydroxy-phenyl)-isoxazole-3-carboxylic acid ethylamide SST0090AA1

This compound was obtained following the procedure of step vii as described in example 1 starting from 4-nitro-5-(5-chloro-2,4-dihydroxy-phenyl)-isoxazole-3-carboxylic acid ethylamide and followed by standard benzyl deprotection using the reaction conditions described in example 1-step ix.

$^1$H NMR (400 MHz DMSO), δ: 1.11 (t, J=7.6 Hz, 3H), 3.26-3.30 (m, 2H), 6.67 (s, 1H), 7.35 (s, 1H), 8.58 (t, J=5.6 Hz, 1H), 8.75 (s, 1H), 10.15 (s, 1H), 10.70 (s, 1H).
$^{13}$C NMR (100 MHz DMSO), δ: 14.3, 27.4, 33.5, 35.9, 38.3, 38.8, 103.8, 106.1, 113.4, 129.3, 139.8, 155.0, 155.3, 155.6, 158.4, 176.0.
[M+H]$^+$ 460.2/461.3.

Biological Results
Materials and Methods
Cytotoxicity Assay:

To evaluate the effect of the compounds on cells survival, the sulphorodamine B test was used. To test the effects of the compounds on cell growth, NCI-H460 non-small cell lung carcinoma cells were used. Tumour cells were grown in RPMI 1640 containing 10% fetal bovine serum (GIBCO).

Tumour cells were seeded in 96-well tissue culture plates at approximately 10% confluence and were allowed to attach and recover for at least 24 h. Varying concentrations of the drugs were then added to each well to calculate their $IC_{50}$ value (the concentration which inhibits the 50% of cell survival). The plates were incubated at 37° C. for 72 h. At the end of the treatment, the plates were washed by removal of the supernatant and addition of phosphate buffered saline (PBS) 3 times. 200 μl PBS and 50 μl of cold 80% trichloroacetic acid (TCA) were added. The plates were incubated on ice for at least 1 h. TCA was removed, the plates were washed 3 times by immersion in distilled water and dried on paper and at 40° C. for 5 min. Then 200 μl of 0.4% sulphorodamine B in 1% acetic acid were added. The plates were incubated at RT for 30 min. Sulphorodamine B was removed, the plates were washed by immersion in 1% acetic acid for 3 times, then they were dried on paper and at 40° C. for 5 min. Then, 200 μl Tris 10 mM were added, the plates were kept under stirring for 20 min. The cell survival was determined as optical density by a Multiskan spectrofluorimeter at 540 nm. The amount of cells killed was calculated as the percentage decrease in sulphorodamine B binding compared with control cultures.

The $IC_{50}$ values were calculated with the "ALLFIT" program.
Fluorescence Polarization (FP)

GM-BODIPY (PerkinElmer, CUSN60342000MG) was previously dissolved in DMSO to obtain 10 mM stock solutions and kept at −20° C. until use.

Hsp90 (Stressgen, SPP-776), was previously dissolved in assay buffer (HFB) containing 20 mM HEPES (K) pH 7.3, 50 mM KCl, 5 mM $MgCl_2$, 20 mM $Na_2MoO4$ and 0.01% NP40 to form 2.2 μM stock solutions and kept at −80° C. until use.

The compounds were previously dissolved in DMSO to obtain stock solutions and kept at −20° C. The day of experiment, the compounds were prepared by serial dilutions in HFB. Before each use, 0.1 mg/ml Bovine Gamma globulin and 2 mM DTT were freshly added.

Fluorescence Polarization (FP) was performed in Opti-Plate™-96F well plates (Perkin Elmer, Zaventem, Belgium) using a plate reader (Wallac Envision 2101 multilabel reader, Perkin Elmer, Zaventem, Belgium). To evaluate the binding affinity of the molecules, 50 µl of the GM-BODIPY solution (100 nM) were added to 125 nM of Hsp90 in the presence of 5 µl of the test compounds at increasing concentrations. The plate was mixed on a shaker at 4° C. for 4 hours, and the FP values in mP (millipolarization units) were recorded. The $IC_{50}$ values were calculated as the inhibitor concentration where 50% of the tracer is displaced; each data point is the result of the average of triplicate wells, and was determined from a plot using nonlinear least-squares analysis. Curve fitting was performed using Prism GraphPad software program (GraphPad software, Inc., San Diego, Calif.).

The antiproliferative activity of novel Hsp90 inhibitors was evaluated on NCI-H460 non-small cell lung carcinoma cells and on a human epithelial carcinoma cell line A431. Most of the molecules evaluated for their binding affinity on Hsp90 catalytic site revealed to be potent with submicromolar $IC_{50}$ values (table 1). According to this high specificity for the Hsp90 catalytic ATP-binding site, all compounds resulted to possess a strong antiproliferative activity.

TABLE 1

| Examples | SST Nbr | F.P. binding assay IC50 (µM) | Cytotoxicity NCI-H460 IC50 (µM) | Cytotoxicity A431 IC50 (µM) |
|---|---|---|---|---|
| 1 | SST0072AA1 | ++++ | ++ | ++ |
| 2 | SST0081AA1 | +++ | ++ | +++ |
| 3 | SST0100AA1 | +++ | ++ | +++ |
| 4 | SST0101AA1 | +++ | +++ | +++ |
| 5 | SST0091AA1 | ++++ | +++ | ++++ |
| 6 | SST0093AA1 | +++ | +++ | +++ |
| 7 | SST0098AA1 | +++ | ++ | +++ |
| 8 | SST0092AA1 | ++++ | +++ | ++++ |
| 9 | SST0099AA1 | +++ | +++ | +++ |
| 10 | SST0102AA1 | +++ | ++ | +++ |
| 11 | SST0107AA1 | +++ | ++++ | NT |
| 12 | SST0113AA1 | ++++ | ++++ | NT |
| 13 | SST0114AA1 | ++++ | ++++ | NT |
| 14 | SST0115AA1 | ++++ | ++++ | ++++ |
| 15 | SST0116AA1 | +++ | +++ | NT |
| 16 | SST0203AA1 | +++ | ++ | +++ |
| 17 | SST0220AA1 | ++++ | +++ | +++ |
| 18 | SST0201CL1 | ++++ | ++++ | ++++ |
| 19 | SST0221AA1 | +++ | ++++ | ++++ |
| 20 | SST0222AA1 | +++ | ++ | ++ |
| 21 | SST0223AA1 | +++ | ++++ | ++++ |
| 22 | SST0211AA1 | ++++ | ++ | ++ |
| 23 | SST0226AA1 | ++++ | ++++ | NT |
| 24 | SST0227AA1 | ++++ | +++ | NT |
| 25 | SST0228CL1 | ++++ | ++ | NT |
| 26 | SST0229CL1 | ++++ | ++ | NT |
| 27 | SST0207AA1 | +++ | ++ | ++ |
| 28 | SST0206AA1 | +++ | ++ | ++ |
| 29 | SST0208AA1 | +++ | ++ | ++ |
| 30 | SST0209AA1 | ++ | ++ | ++ |
| 31 | SST0210AA1 | ++++ | ++ | ++ |
| 32 | SST0212AA1 | +++ | ++ | ++ |
| 33 | SST0204AA1 | +++ | ++ | +++ |
| 34 | SST0205AA1 | NA | NA | NA |

[++++] [$IC_{50}$] < 100 nM; [+++] 100 nM < [$IC_{50}$] < 1 µM; [++] 1 µM < [$IC_{50}$] < 10 µM; [+] 10 µM < [$IC_{50}$]; NA: not active; NT: not tested The FP binding assay $IC_{50}$ values were calculated as the inhibiting concentration where 50% of the tracer was displaced; each data point is the result of the average of triplicate wells, and were determined from a plot using nonlinear least-squares analysis. Curve fitting was performed using Prism GraphPad software program (GraphPad software, Inc., San Diego, Calif.).

The antiproliferative $IC_{50}$ was evaluated as drug concentration required for 50% reduction of cell growth as compared with untreated controls after 72-h exposure to the drug. The $IC_{50}$±SD values reported were calculated by ALLFIT program.

The invention claimed is:
1. A compound having the general formula I

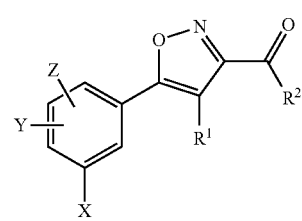

Formula I wherein,
X is halogen, alkyl, alkenyl, haloalkyl, aryl, heteroaryl, benzyl, amino, alkylamino, or aminocarbonyl;
Y and Z, the same or different, are halogen, nitro, haloalkyl, $R^3$, $OR^3$, amino, alkylamino, or aminocarbonyl;
$R^3$ is hydrogen or alkyl;
$R^1$ is NHC(=D)E$R^4$ or NR$^5$R$^6$;
D is O or S;
E is O, NR$^7$ or is absent;
$R^7$ is hydrogen or alkyl;
$R^4$ is alkyl optionally substituted once with alkoxy or amino; alkenyl, aryl optionally substituted once or more with alkoxy, halo or heterocycloalkylalkyl; cycloalkyl optionally substituted once or more with alkyl, haloalkyl, alkoxy, amino or aminoalkyl; norbornyl, adamantyl, heteroaryl optionally substituted once or more with alkyl, alkylaminocarbonyl; heterocycloalkyl optionally substituted once or more with alkyl; or heterocycloalkylalkyl optionally substituted once or more with alkyl;
$R^5$ and $R^6$ independently are hydrogen, alkyl, cycloalkyl, heterocycloalkyl optionally substituted once or more with alkyl; alkenyl, benzyl, aryl, arylalkyl optionally substituted with alkoxy; heteroaryl, heteroarylalkyl optionally substituted once or more with alkyl, hydroxyalkyl, alkoxy, alkoxycarbonyl; or $R^5$ and $R^6$ taken together with the nitrogen atom to which they are attached can form an optionally substituted 5 to seven-membered heterocycle ring, which optional substitution being halogen, hydroxyl, alkoxyl, alkyl, aryl, arylalkyl, alkylcarbonyl or aminocarbonyl;
$R^2$ is NR$^8$R$^9$;
$R^8$ and $R^9$, the same or different are chosen from H, alkyl optionally substituted with halogen;
haloalkyl, aryl, cycloalkyl, heterocycloalkyl and heteroaryl; or $R^8$ and $R^9$, taken together with the nitrogen atom to which they are attached, form a heterocycle that may contain one or two further heteroatoms selected from O, S or N and which can optionally be substituted once or twice with alkyl or halogen; and
their tautomers, their geometrical isomers, their optically active forms such as enantiomers, diastereomers and their racemate forms, as well as their pharmaceutically acceptable salts thereof.
2. A compound according to claim 1, wherein $R^1$ represents NHC(=D)E$R^4$.

3. A compound according to claim 1, wherein X is halogen or alkyl.

4. A compound according to claim 1 selected from the group consisting of 4-acetylamino-5-(5-chloro-2,4-dihydroxy-phenyl)-isoxazole-3-carboxylic acid ethylamide 5-(5-chloro-2,4-dihydroxy-phenyl)-4-(4-methoxy-benzoylamino)-isoxazole-3-carboxylic acid ethylamide; 5-(5-chloro-2,4-dihydroxy-phenyl)-4-(3,4-dimethoxy-benzoylamino)-isoxazole-3-carboxylic acid ethylamide; 5-(5-chloro-2,4-dihydroxy-phenyl)-4-(3,4,5-trimethoxy-benzoylamino)-isoxazole-3-carboxylic acid ethylamide; 5-(5-chloro-2,4-dihydroxy-phenyl)-4-(2,2-dimethyl-propionylamino)-isoxazole-3-carboxylic acid ethylamide; 4-[(adamantane-1-carbonyl-amino]-5-(5-chloro-2,4-dihydroxy-phenyl-isoxazole-3-carboxylic acid ethylamide; 4-acryloylamino-5-(5-chloro-2,4-dihydroxy-phenyl)-isoxazole-3-carboxylic acid ethylamide; 5-(5-chloro-2,4-dihydroxy-phenyl)-4-[(3-methyl-thiophene-2-carbonyl)-amino]-isoxazole-3-carboxylic acid ethylamide; 5-(5-chloro-2,4-dihydroxy-phenyl)-4-(3-morpholin-4-yl-propionylamino)-isoxazole-3-carboxylic acid ethylamide; 4-(4-bromo-benzoylamino)-5-(5-chloro-2,4-dihydroxy-phenyl)-isoxazole-3-carboxylic acid ethylamide; 5-(2,4-dihydroxy-5-isopropyl-phenyl)-4-(4-methoxy-benzoylamino)-isoxazole-3-carboxylic acid ethylamide; 4-acetylamino-5-(2,4-dihydroxy-5-isopropyl-phenyl)-isoxazole-3-carboxylic acid ethylamide; 5-(2,4-dihydroxy-5-isopropyl-phenyl)-4-(2,2-dimethyl-propionylamino)-isoxazole-3-carboxylic acid ethylamide; 5-(2,4-dihydroxy-5-isopropyl-phenyl)-4-[(3-methyl-thiophene-2-carbonyl)-amino]-isoxazole-3-carboxylic acid ethylamide; 5-(2,4-dihydroxy-5-isopropyl-phenyl)-4-(3-morpholin-4-yl-propionylamino)-isoxazole-3-carboxylic acid ethylamide; 4-(3-(4-methylpiperazin-1-yl)propanamido)-N-ethyl-5-(2,4-dihydroxy-5-isopropylphenyl)-isoxazole-3-carboxamide; 1H-indole-6-carboxylic acid [5-(2,4-dihydroxy-5-isopropyl-phenyl)-3-ethyl carbamoyl-isoxazol-4-yl]-amide; 5-(2,4-dihydroxy-5-isopropyl-phenyl)-4-(4-morpholin-4-yl-methyl-benzoyl amino)-isoxazole-3-carboxylic acid ethylamide hydrochloride; 4-(cyclohexanecarbonyl-amino)-5-(2,4-dihydroxy-5-isopropyl-phenyl-isoxazole-3-carboxylic acid ethylamide; 5-(2,4-dihydroxy-5-isopropyl-phenyl)-4-[(trans-4-pentyl-cyclohexanecarbonyl)-amino]-isoxazole-3-carboxylic acid ethylamide; 5-(2,4-dihydroxy-5-isopropyl-phenyl)-4-[(4-trifluoromethyl-cyclohexane carbonyl)-amino]-isoxazole-3-carboxylic acid ethylamide; $N^5$-(3-(ethylcarbamoyl)-5-(2,4-dihydroxy-5-isopropylphenyl)-isoxazol-4-yl)-$N^3$-ethylisoxazole-3,5-dicarboxamide; 5-(2,4-dihydroxy-5-isopropyl-phenyl)-4-[(4-methoxy-cyclohexanecarbonyl)-amino]-isoxazole-3-carboxylic acid ethylamide; 4-[(4-tert-butyl-cyclohexanecarbonyl)-amino]-5-(2,4-dihydroxy-5-isopropyl-phenyl)-isoxazole-3-carboxylic acid ethylamide; 4-[(4-amino-cyclohexanecarbonyl)-amino]-5-(2,4-dihydroxy-5-isopropyl-phenyl)-isoxazole-3-carboxylic acid ethylamide; 4-[(4-aminomethyl-cyclohexanecarbonyl)-amino]-5-(2,4-dihydroxy-5-isopropyl-phenyl)-isoxazole-3-carboxylic acid ethylamide; 4-(4-methoxybenzylamino)-5-(5-chloro-2,4-dihydroxyphenyl)-N-ethylisoxazole-3-carboxamide; 4-((3-methylthiophen-2-yl)methylamino)-5-(5-chloro-2,4-dihydroxyphenyl)-N-ethylisoxazole-3-carboxamide; 5-(5-chloro-2,4-dihydroxyphenyl)-4-(cyclohexylamino)-N-ethylisoxazole-3-carboxamide; 4-(1-methylpiperidin-4-ylamino)-5-(5-chloro-2,4-dihydroxyphenyl)-N-ethylisoxazole-3-carboxamide; Methyl 5-43-(ethylcarbamoyl)-5-(5-chloro-2,4-dihydroxyphenyl)isoxazol-4-ylamino)methyl)isoxazole-3-carboxylate; 4-(3-(hydroxymethyl)isoxazol-5-yl)methylamino)-5-(5-chloro-2,4-dihydroxyphenyl)-N-ethylisoxazole-3-carboxamide; 4-(4-methoxybenzamido)-5-(5-chloro-2,4-dihydroxyphenyl)-N-(2,2,2-trifluoroethyl)-isoxazole-3-carboxamide; 4-(4-methoxybenzamido)-5-(5-chloro-2,4-dihydroxyphenyl)-isoxazol-3-yl)-(3,3-difluoroazetidin-lyl)-methanone and 5-(5 chloro-2,4-dihydroxy-phenyl)-4-(4-methoxy-benzoylamino)-isoxazol-3-yl)-(4-methylpiperazin-1-yl)-methanone.

5. A pharmaceutical composition comprising at least one compound according to claim 1 as active ingredient together with a pharmaceutically acceptable excipient.

6. A process for preparing a pharmaceutical composition comprising mixing at least one compound according to claim 1 or one of its pharmaceutically acceptable salts with a pharmaceutically acceptable carrier.

7. Process for synthesizing compounds of claim 1, where $R^1$ is NHC(=D)ER$^4$, D and R$^4$ being as defined in claim 1 and E is absent, comprising the step of reacting compounds of formula II

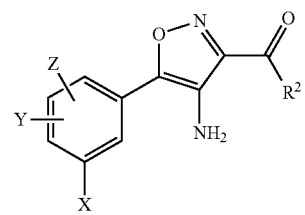

Formula II wherein X, Y, Z and $R^2$ are as described in claim 1, with an acyl chloride of formula ClCOR$^4$ and subsequently with Lawesson's reagent in case D is S.

8. Process for synthesizing compounds of claim 1, where $R^1$ is NR$^5$R$^6$, R$^5$ and R$^6$ being alkyl, alkenyl, cycloalkyl, benzyl, arylalkyl, heteroarylalkyl or heterocycloalkyl or one of R$^5$ and R$^6$ is H, comprising the step of reacting compounds of formula II, wherein X, Y, Z and R$^2$ are as described in claim 1, with one or more equivalents of a compound of formula R—CHO or R'=O (with the meaning of ketone), where the moieties R—C and R' have the meaning of R$^5$ or R$^6$ as described in claim 1, in a polar solvent in the presence of an acid and of a reducing agent.

9. Process of claim 8 wherein the acid is AcOH and wherein the reducing agent is NaCNBH$_4$.

10. A compound of formula VII

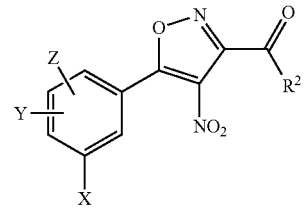

Formula VII as an intermediate in the synthesis of compounds according to claim 1
having the general formula I

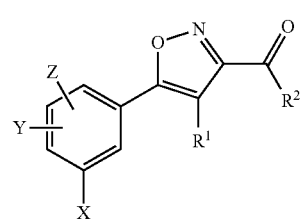

Formula I wherein,
X is halogen, alkyl, alkenyl, haloalkyl, aryl, heteroaryl, benzyl, amino, alkylamino, or aminocarbonyl;

Y and Z, the same or different, are halogen, nitro, haloalkyl, $R^3$, $OR^3$, amino, alkylamino, or aminocarbonyl;

$R^3$ is hydrogen or alkyl;

$R^1$ is NHC(=D)ER$^4$ or NR$^5$R$^6$;

D is O or S;

E is O, NR$^7$ or is absent;

$R^7$ is hydrogen or alkyl;

$R^4$ is alkyl optionally substituted once with alkoxy or amino; alkenyl, aryl optionally substituted once or more with alkoxy, halo or heterocycloalkylalkyl; cycloalkyl optionally substituted once or more with alkyl, haloalkyl, alkoxy, amino or aminoalkyl; norbornyl, adamantyl, heteroaryl optionally substituted once or more with alkyl, alkylaminocarbonyl; heterocycloalkyl optionally substituted once or more with alkyl; or heterocycloalkylalkyl optionally substituted once or more with alkyl;

$R^5$ and $R^6$ independently are hydrogen, alkyl, cycloalkyl, heterocycloalkyl optionally substituted once or more with alkyl; alkenyl, benzyl, aryl, arylalkyl optionally substituted with alkoxy; heteroaryl, heteroarylalkyl optionally substituted once or more with alkyl, hydroxyalkyl, alkoxy, alkoxycarbonyl; or $R^5$ and $R^6$ taken together with the nitrogen atom to which they are attached can form an optionally substituted 5 to seven-membered heterocycle ring, which optional substitution being halogen, hydroxyl, alkoxyl, alkyl, aryl, arylalkyl, alkylcarbonyl or aminocarbonyl;

$R^2$ is NR$^8$R$^9$;

$R^8$ and $R^9$, the same or different are chosen from H, alkyl optionally substituted with halogen; haloalkyl, aryl, cycloalkyl, heterocycloalkyl and heteroaryl; or $R^8$ and $R^9$, taken together with the nitrogen atom to which they are attached, form a heterocycle that may contain one or two further heteroatoms selected from 0, S or N and which can optionally be substituted once or twice with alkyl or halogen; and their tautomers, their geometrical isomers, their optically active forms such as enantiomers, diastereomers and their racemate forms, as well as their pharmaceutically acceptable salts thereof.

11. Process for synthesizing compounds of formula VII

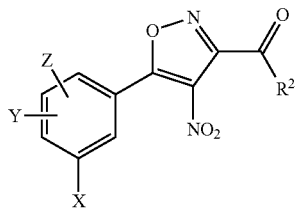

Formula VII wherein X, Y, Z and $R^2$ are as described in claim 10 comprising the step of reacting compounds of formula VI

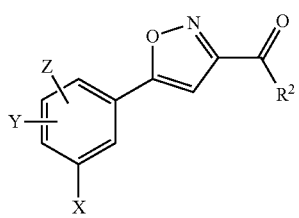

Formula VI wherein X, Y, Z and $R^2$ are as described in claim 10 above, with HNO$_3$/Ac$_2$O.

12. A compound of formula II

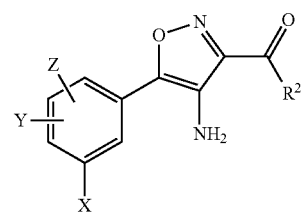

Formula II as an intermediate in the synthesis of compounds having the general formula I

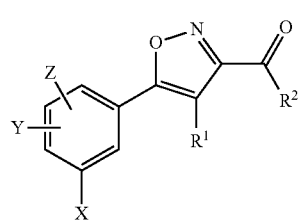

Formula I wherein,

X is halogen, alkyl, alkenyl, haloalkyl, aryl, heteroaryl, benzyl, amino, alkylamino, or aminocarbonyl;

Y and Z, the same or different, are halogen, nitro, haloalkyl, $R^3$, $OR^3$, amino, alkylamino, or aminocarbonyl;

$R^3$ is hydrogen or alkyl;

$R^1$ is NHC(=D)ER$^4$ or NR$^5$R$^6$;

D is O or S;

E is O, NR$^7$ or is absent;

$R^7$ is hydrogen or alkyl;

$R^4$ is alkyl optionally substituted once with alkoxy or amino; alkenyl, aryl optionally substituted once or more with alkoxy, halo or heterocycloalkylalkyl; cycloalkyl optionally substituted once or more with alkyl, haloalkyl, alkoxy, amino or aminoalkyl; norbornyl, adamantyl, heteroaryl optionally substituted once or more with alkyl, alkylaminocarbonyl; heterocycloalkyl optionally substituted once or more with alkyl; or heterocycloalkylalkyl optionally substituted once or more with alkyl;

$R^5$ and $R^6$ independently are hydrogen, alkyl, cycloalkyl, heterocycloalkyl optionally substituted once or more with alkyl; alkenyl, benzyl, aryl, arylalkyl optionally substituted with alkoxy; heteroaryl, heteroarylalkyl optionally substituted once or more with alkyl, hydroxyalkyl, alkoxy, alkoxycarbonyl; or $R^5$ and $R^6$ taken together with the nitrogen atom to which they are attached can form an optionally substituted 5 to seven-membered heterocycle ring, which optional substitution being halogen, hydroxyl, alkoxyl, alkyl, aryl, arylalkyl, alkylcarbonyl or aminocarbonyl;

$R^2$ is NR$^8$R$^9$;

$R^8$ and $R^9$, the same or different are chosen from H, alkyl optionally substituted with halogen;

haloalkyl, aryl, cycloalkyl, heterocycloalkyl and heteroaryl; or $R^8$ and $R^9$, taken together with the nitrogen atom to which they are attached, form a heterocycle that may contain one or two further heteroatoms selected from O, S or N and which can optionally be substituted once or twice with alkyl or halogen; and their tautomers, their geometrical isomers, their optically active forms such as enantiomers, diastereomers and their racemate forms, as well as their pharmaceutically acceptable salts thereof.

13. Process for synthesizing compounds of formula II

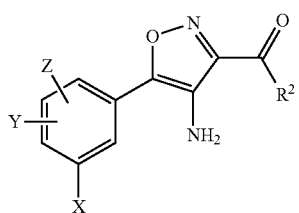

Formula II wherein X, Y, Z and $R^2$ are as described in claim 12 comprising the step of reacting compounds of formula VII as described in claim 12 with $Zn/NH_4Cl$ in a mixture of $THF/H_2O$.

14. Method of treating a pathological state for which the modulation of Hsp90 activity would result in improving the health of the patient, comprising administering a therapeutically effective amount of a compound of claim 1 to patient in need thereof, wherein the pathological state is inflammatory disease, autoimmune disease, cerebral ischemia, parasitemia, malaria, Parkinson disease, Huntington disease, Alzheimer disease, dementia with Lewy bodies, amyotrophic lateral sclerosis, spinal and bulbar muscular atrophy, spinocerebellar ataxia, cancer of the breasts, pancreas, lung, pleura, peritoneum, face and neck, bladder, brain, prostate, ovaries, eyes or a metastatic cancer.

15. Method of claim 14, wherein said compound is administered at a dose of from 0.01 mg/kg to 100 mg/kg.

16. Method of claim 15, wherein said compound is administered at a dose of from 0.05 mg/kg to 50 mg/kg.

* * * * *

UNITED STATES PATENT AND TRADEMARK OFFICE
CERTIFICATE OF CORRECTION

PATENT NO.      : 8,383,616 B2                                       Page 1 of 1
APPLICATION NO. : 13/001652
DATED           : February 26, 2013
INVENTOR(S)     : Giannini et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 96 days.

Signed and Sealed this
First Day of September, 2015

Michelle K. Lee
*Director of the United States Patent and Trademark Office*